(12) United States Patent
Zhang et al.

(10) Patent No.: US 11,123,433 B2
(45) Date of Patent: Sep. 21, 2021

(54) HYDROPHOBICALLY MODIFIED POLYPEPTOIDS AND USES THEREOF

(71) Applicants: BOARD OF SUPERVISORS OF LOUISIANA STATE UNIVERSITY AND AGRICULTURAL AND MECHANICAL COLLEGE, Baton Rouge, LA (US); THE ADMINISTRATORS OF THE TULANE EDUCATIONAL FUND, New Orleans, LA (US)

(72) Inventors: Donghui Zhang, Baton Rouge, LA (US); Vijay John, Destrehan, LA (US); Yueheng Zhang, New Orleans, LA (US); Sunting Xuan, Baton Rouge, LA (US)

(73) Assignees: BOARD OF SUPERVISORS OF LOUISIANA STATE UNIVERSITY, Baton Rouge, LA (US); THE ADMINISTRATORS OF THE TULANE EDUCATIONAL FUND, New Orleans, LA (US)

( * ) Notice: Subject to any disclaimer, the term of this patent is extended or adjusted under 35 U.S.C. 154(b) by 105 days.

(21) Appl. No.: 16/306,429

(22) PCT Filed: Feb. 7, 2017

(86) PCT No.: PCT/US2017/016817
§ 371 (c)(1),
(2) Date: Nov. 30, 2018

(87) PCT Pub. No.: WO2017/209805
PCT Pub. Date: Dec. 7, 2017

(65) Prior Publication Data
US 2019/0185622 A1 Jun. 20, 2019

Related U.S. Application Data

(60) Provisional application No. 62/344,083, filed on Jun. 1, 2016.

(51) Int. Cl.
*C08G 69/00* (2006.01)
*A61K 47/34* (2017.01)
*A01N 37/18* (2006.01)

(52) U.S. Cl.
CPC .............. *A61K 47/34* (2013.01); *C08G 69/00* (2013.01); *A01N 37/18* (2013.01)

(58) Field of Classification Search
None
See application file for complete search history.

(56) References Cited

U.S. PATENT DOCUMENTS

2010/0028719 A1  2/2010  Messersmith et al.
2010/0041592 A1  2/2010  Kabanov et al.
(Continued)

FOREIGN PATENT DOCUMENTS

CN    104059223 A  *  9/2014
CN    105199098 A  *  12/2015

OTHER PUBLICATIONS

Lahasky et al (Synthesis and characterization of thermo-responsive polypeptoid bottlebrushes, Polym. Chem., 2014,5, 1418-1426). (Year: 2014).*
(Continued)

*Primary Examiner* — Rachel Kahn
(74) *Attorney, Agent, or Firm* — Thomas | Horstemeyer, LLP

(57) ABSTRACT

A variety of hydrophobically modified polypeptoids are provided. The hydrophobically modified polypeptoids can include a polyamide backbone having a random copolymer
(Continued)

of two or more different types of repeat units, where one or more of the repeat units have nitrogen atom having a hydrophobic substituent attached thereto. Methods of making the hydrophobically modified polypeptoids are also provided, as well as uses of the hydrophobically modified polypeptoids, for example in liposomal drug delivery.

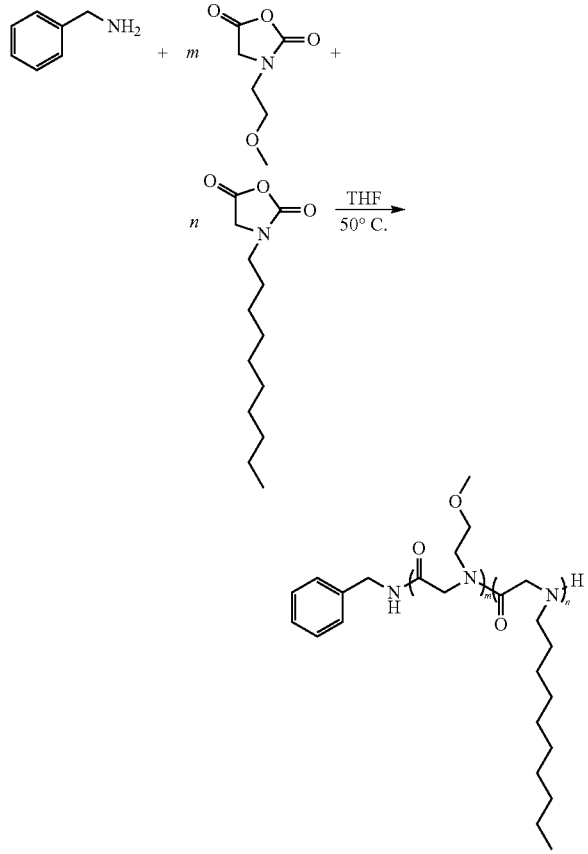

7 Claims, 11 Drawing Sheets

References Cited

U.S. PATENT DOCUMENTS

| | | |
|---|---|---|
| 2012/0046443 A1 | 2/2012 | Zuckermann et al. |
| 2013/0109627 A1 | 5/2013 | Barron et al. |
| 2015/0031743 A1 | 1/2015 | Burkoth et al. |

OTHER PUBLICATIONS

Lahasky et al (Thermoresponsive Poly($\alpha$-peptoid)s: Tuning the Cloud Point Temperatures by Composition and Architecture | ACS Macro Lett. 2012, 1, 580-584). (Year: 2012).*

Li et al (Synthesis and Characterization of Cleavable Core-Cross-Linked Micelles Based on Amphiphilic Block Copolypeptoids as Smart Drug Carriers, Biomacromolecules 2016, 17, 852-861). (Year: 2016).*

Lee et al (Crystallization and Melting Behaviors of Cyclic and Linear Polypeptoids with Alkyl Side Chains, Macromolecules 2013, 46, 8213-8223, and Supporting Information pp. 1-15). (Year: 2013).*

Coelho et al (Drug delivery systems: Advanced technologies potentially applicable in personalized treatments, EPMA Journal (2010) 1:164-209). (Year: 2010).*

International Search Report dated Apr. 13, 2017.

Felsch et al. "Highly Defined Multiblock Copolypeptoids: Pushing the Limits of Living Nucleophilic Ring-Opening Polymerization" Macromolecular Rapid Communications, 2012; 33(19):1708-1713 (doi: 10.1002/marc.201200189) Scheme 1, Roule B; Supporting Information, p. 5, para 3.

Lee et al. "Crystallization and Melting Behaviors of Cyclic and Linear Polypeptoids with Alkyl Side Chains" Macromolecules, 2013; 46(20):8213-8223 (doi: 10.1021/ma401067f) Table 1.

Lobo et al. "Structure/Function Analysis of Peptoid/Lipitoid:DNA Complexes" J Pharm Sci. 2003; 92(9):1905-191B. Whole document.

* cited by examiner

HYDROPHOBICALLY MODIFIED POLYPEPTOIDS AND USES THEREOF

CROSS-REFERENCE TO RELATED APPLICATION

This application is the 35 U.S.C. 0.371 national stage application of PCT Application No. PCT/US2017/016817, filed Feb. 7, 2017, where the PCT claims priority to, and the benefit of U.S. provisional application entitled "HYDROPHOBICALLY MODIFIED POLYPEPTOIDS AS LIPID BASED DRUG DELIVERY AGENTS AND AS ANTIMICROBIALS" having Ser. No. 62/344,083, filed Jun. 1, 2016, both of which are herein incorporated by reference in their entireties.

STATEMENT REGARDING FEDERALLY SPONSORED RESEARCH OR DEVELOPMENT

This invention was made with government support under award DE-SC0012432 awarded by the Department of Energy. The government has certain rights to the invention.

TECHNICAL FIELD

The present disclosure generally relates to the area of pseudo-peptidic polymers and methods of making and uses thereof.

BACKGROUND

Liposome delivery systems have been used as carriers for a variety of compounds, including pharmacologically active compounds, diagnostic agents, and cosmetics. Liposomes have one or more lipid bilayers enclosing one or more aqueous internal compartments, where the compound to be delivered is entrapped in either the aqueous internal spaces, in the lipid bilayer(s), or both, depending on the nature of the compound. Water soluble compounds are readily entrapped in the aqueous internal space(s), and a sufficient quantity to arrive at a meaningful delivery system. Compounds that are poorly water soluble or hydrophobic compounds are not well suited for incorporation into the aqueous internal space(s). Instead, poorly water soluble compounds tend to be incorporated into the lipid bilayer(s), which has certain disadvantages. First, the presence of the compound in the lipid bilayer(s) can destabilize the liposome structure. Second, the quantity of compound that can be incorporated into the lipid bilayer(s) is limited.

There remains a need for improved hydrophobic materials, for example that can be used to entrap hydrophobic drugs for drug delivery and/or that can interact with or stabilize lipid bilayer systems.

SUMMARY

In various embodiments, compositions and methods are provided that overcome one or more of the aforementioned deficiencies. Polypeptoids have been of recent interest in chemical biology due to their highly designable structure and their structural similarity to polypeptides. Unlike polypeptides however, polypeptoids lack extensive hydrogen bonding and backbone chirality due to the N-substitution, leading to a more flexible conformation and an enhanced resistance to proteolysis. Due to backbone degradability, biocompatibility, and processability, polypeptoids are of promise in applications related to drug delivery carriers, tissue engineering materials, and smart coatings. In various embodiments, hydrophobically modified polypeptoids are provided. The hydrophobically modified polypeptoids can interact with lipids and liposomes, for example by disrupting the lipid bilayer or by forming multilamellar structures on the surface of a liposome. The hydrophobically modified polypeptoids can be used to deliver hydrophobic drugs.

In some embodiments, a hydrophobically modified polypeptoid is provided having a polyamide backbone including a random copolymer of two or more different types of repeat units, wherein one or more of the repeat units has a nitrogen atom in the backbone having a hydrophobic substituent attached thereto. The hydrophobically modified polypeptoid can be a poly($\alpha$-peptoid), a poly($\beta$-peptoid), or a poly($\gamma$-peptoid). The hydrophobically modified polypeptoids provided herein can be made with varying degrees of hydrophobic modification. For example, in some embodiments about 30% to 95% of the repeat units have a structure selected from the group Formula A1, Formula A2, and Formula A3,

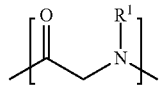

Formula A1

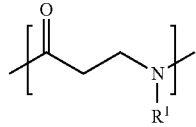

Formula A2

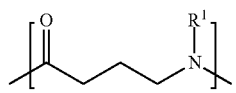

Formula A3 wherein each occurrence of $R^1$ is independently a hydrogen or a substituted or unsubstituted alkoxy, aryloxy, alkyl, alkenyl, alkynyl, aryl, arylalkyl, carbamate, carboxy, cycloalkyl, ester, ether, haloalkyl, heteroaryl, heterocyclyl, or ketone substituent having from 1 to 6 carbon atoms. In some embodiments about 5% to 50% of the repeat units have a structure selected from Formula B1, Formula B2, and Formula B3,

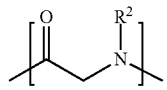

Formula B1

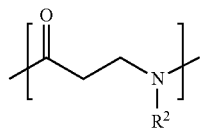

Formula B2

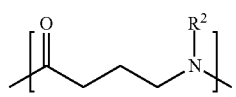

Formula B3 wherein each occurrence of $R^2$ is independently a substituted or unsubstituted alkoxy, aryloxy, alkyl, alkenyl, alkynyl, aryl, arylalkyl, carbamate, carboxy, cycloalkyl, ester, ether, haloalkyl, heteroaryl, heterocyclyl, or ketone group having from 6 to 30 carbon atoms.

In some embodiments, the hydrophobically modified polypeptoid is a random copolymer having a structure according to Formula I or a derivative thereof:

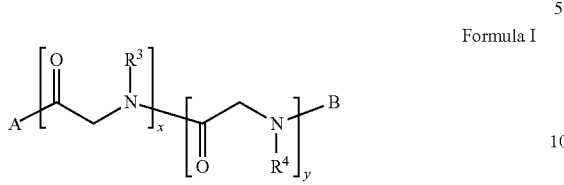

Formula I where x and y are positive integers, A is a substituted or unsubstituted aryl group, B is a hydrogen, and where $R^3$ and $R^4$ are as described above. In one or more aspects, x+y is about 12 to 300. For example, x can be about 50 to 80, and y can be about 15 to 25. In one or more aspects, each occurrence of $R^3$ is hydrogen or a substituted or unsubstituted alkyl or alkoxy substituent having from 1 to 6 carbon atoms. In one or more aspects, each occurrence of $R^4$ is an alkoxy, alkyl, or heteroalkyl substituent having from 12 to 18 carbon atoms. For example, in some aspects, $R^3$ is a methoxyethyl substituent, and $R^4$ is a lauryl, stearyl, behenyl, or cetyl substituent.

A variety of methods are provided for making the hydrophobically modified polypeptoids described herein. In one or more embodiments, the methods include polymerizing a quantity of two or more different N-substituted N-carboxyanhydride monomers at an elevated temperature to produce the hydrophobically modified polypeptoid, wherein at least one of the N-substituted N-carboxyanhydride monomers has a hydrophobic substituent on the nitrogen atom. The hydrophobic substituent can be selected from substituted and unsubstituted alkoxy, aryloxy, alkyl, alkenyl, alkynyl, aryl, arylalkyl, carbamate, carboxy, cycloalkyl, ester, ether, haloalkyl, heteroaryl, heterocyclyl, and ketone groups having from 6 to 30 carbon atoms. In one or more aspects, the elevated temperature is about 40° C. to 60° C.

The hydrophobically modified polypeptoids can be used various applications, several of which are contemplated herein. In one or more embodiments, the hydrophobically modified polypeptoids can be used in an antimicrobial compositions. For example, a sufficient concentration of the hydrophobically modified polypeptoids can be applied in an antimicrobial composition to disrupt bacterial cytoplasmic membranes. In various embodiments, the hydrophobically modified polypeptoids can be used to deliver one or more hydrophobic drugs. For example, a lipid raft is provided including a plurality of hydrophobically modified polypeptoids and a hydrophobic drug. The lipid raft can also include one or more lipids. In some embodiments, liposomal particles are provided including a liposome having a lipid bilayer forming an interior region and an exterior surface, a hydrophilic drug in the interior region, and a plurality of hydrophobically modified polypeptoids on the exterior surface of the liposome. A hydrophobic drug can further be provided on the exterior surface, e.g. encapsulated within the hydrophobically modified polypeptoids on the exterior surface. The liposomes can be multilamellar liposomes.

Other systems, methods, features, and advantages of hydrophobically modified polypeptoids and methods of making and uses thereof will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Further aspects of the present disclosure will be readily appreciated upon review of the detailed description of its various embodiments, described below, when taken in conjunction with the accompanying drawings.

DETAILED DESCRIPTION

Figure 1:
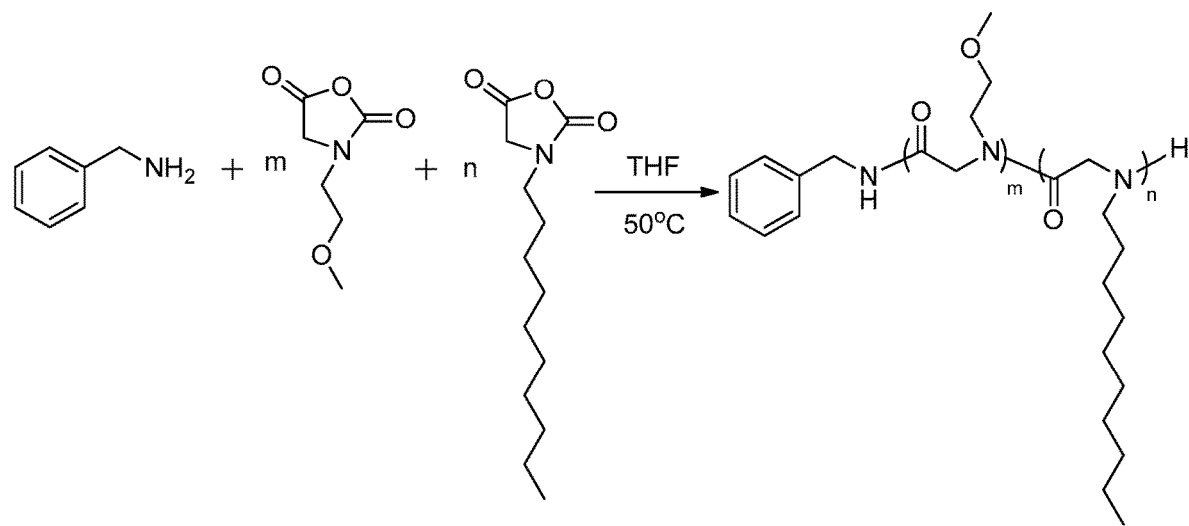
FIG. 1 overview of synthetic scheme for synthesis of PNMeOEtG$_{74}$-r-PNDG$_{26}$ and PNMeOEtG$_{89}$-r-PNDG$_{9}$.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting. The skilled artisan will recognize many variants and adaptations of the embodiments described herein. These variants and adaptations are intended to be included in the teachings of this disclosure and to be encompassed by the claims herein.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

Although any methods and materials similar or equivalent to those described herein can also be used in the practice or testing of the present disclosure, the preferred methods and materials are now described. Functions or constructions well-known in the art may not be described in detail for brevity and/or clarity. Embodiments of the present disclosure will employ, unless otherwise indicated, techniques of nanotechnology, organic chemistry, material science and engineering and the like, which are within the skill of the art. Such techniques are explained fully in the literature.

It should be noted that ratios, concentrations, amounts, and other numerical data can be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to about 5%" should be interpreted to include not only the explicitly recited values of about 0.1% to about 5%, but also include individual values (e.g., 1%, 2%, 3%, and 4%) and the sub-ranges (e.g., 0.5%, 1.1%, 2.2%, 3.3%, and 4.4%) within the indicated range. Where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In some embodiments, the term "about" can include traditional rounding according to significant figures of the numerical value. In addition, the phrase "about 'x' to 'y'", where 'x' and 'y' are numerical values, includes "about 'x' to about 'y'".

Definitions

Unless defined otherwise, all technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used.

The term "biocompatible", as used herein, refers to a material that along with any metabolites or degradation products thereof that are generally non-toxic to the recipient and do not cause any significant adverse effects to the recipient. Generally speaking, biocompatible materials are materials which do not elicit a significant inflammatory or immune response when administered to a patient.

The term "biodegradable" as used herein, generally refers to a material that will degrade or erode under physiologic conditions to smaller units or chemical species that are capable of being metabolized, eliminated, or excreted by the subject. The degradation time is a function of composition and morphology. Degradation times can be from hours to weeks.

The term "pharmaceutically acceptable", as used herein, refers to compounds, materials, compositions, and/or dosage forms that are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the U.S. Food and Drug Administration. A "pharmaceutically acceptable carrier", as used herein, refers to all components of a pharmaceutical formulation that facilitate the delivery of the composition in vivo. Pharmaceutically acceptable carriers include, but are not limited to, diluents, preservatives, binders, lubricants, disintegrators, swelling agents, fillers, stabilizers, and combinations thereof.

The term "molecular weight", as used herein, generally refers to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

The term "small molecule", as used herein, generally refers to an organic molecule that is less than 2000 g/mol in molecular weight, less than 1500 g/mol, less than 1000 g/mol, less than 800 g/mol, or less than 500 g/mol. Small molecules are non-polymeric and/or non-oligomeric.

The term "hydrophilic", as used herein, refers to substances that have strongly polar groups that readily interact with water.

The term "hydrophobic", as used herein, refers to substances that lack an affinity for water; tending to repel and not absorb water as well as not dissolve in or mix with water.

The term "lipophilic", as used herein, refers to compounds having an affinity for lipids.

The term "amphiphilic", as used herein, refers to a molecule combining hydrophilic and lipophilic (hydrophobic) properties. "Amphiphilic material" as used herein refers to a material containing a hydrophobic or more hydrophobic oligomer or polymer (e.g., biodegradable oligomer or polymer) and a hydrophilic or more hydrophilic oligomer or polymer.

The term "reactive coupling group", as used herein, refers to any chemical functional group capable of reacting with a second functional group to form a covalent bond. The selection of reactive coupling groups is within the ability of the skilled artisan. Examples of reactive coupling groups can include primary amines (—$NH_2$) and amine-reactive linking groups such as isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, and fluorophenyl esters. Most of these conjugate to amines by either acylation or alkylation. Examples of reactive coupling groups can include aldehydes (—COH) and aldehyde reactive linking groups such as hydrazides, alkoxyamines, and primary amines. Examples of reactive coupling groups can include thiol groups (—SH) and sulfhydryl reactive groups such as maleimides, haloacetyls, and pyridyl disulfides. Examples of reactive coupling groups can include photoreactive coupling groups such as aryl azides or diazirines. The coupling reaction may include the use of a catalyst, heat, pH buffers, light, or a combination thereof.

The term "protective group", as used herein, refers to a functional group that can be added to and/or substituted for another desired functional group to protect the desired functional group from certain reaction conditions and selectively removed and/or replaced to deprotect or expose the desired functional group. Protective groups are known to the skilled artisan. Suitable protective groups may include those described in Greene, T. W. and Wuts, P. G. M., Protective Groups in Organic Synthesis, (1991). Acid sensitive protective groups include dimethoxytrityl (DMT), tert-butylcarbamate (tBoc) and trifluoroacetyl (tFA). Base sensitive protective groups include 9-fluorenylmethoxycarbonyl (Fmoc), isobutyryl (iBu), benzoyl (Bz) and phenoxyacetyl (pac). Other protective groups include acetamidomethyl, acetyl, tert-amyloxycarbonyl, benzyl, benzyloxycarbonyl, 2-(4-biphenylyl)-2-propyloxycarbonyl, 2-bromobenzyloxycarbonyl, tert-butyl, tert-butyloxycarbonyl, 1-carbobenzoxamido-2,2,2-trifluoroethyl, 2,6-dichlorobenzyl, 2-(3,5-dimethoxyphenyl)-2-propyloxycarbonyl, 2,4-dinitrophenyl, dithiasuccinyl, formyl, 4-methoxybenzenesulfonyl, 4-methoxybenzyl, 4-methylbenzyl, o-nitrophenylsulfenyl, 2-phenyl-2-propyloxycarbonyl, α-2,4,5-tetramethylbenzyloxycarbonyl, p-toluenesulfonyl, xanthenyl, benzyl ester, N-hydroxysuccinimide ester, p-nitrobenzyl ester, p-nitrophenyl ester, phenyl ester, p-nitrocarbonate, p-nitrobenzylcarbonate, trimethylsilyl and pentachlorophenyl ester.

The term "activated ester", as used herein, refers to alkyl esters of carboxylic acids where the alkyl is a good leaving group rendering the carbonyl susceptible to nucleophilic attack by molecules bearing amino groups. Activated esters are therefore susceptible to aminolysis and react with amines to form amides. Activated esters contain a carboxylic acid ester group —$CO_2R$ where R is the leaving group.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups.

In some embodiments, a straight chain or branched chain alkyl has 30 or fewer carbon atoms in its backbone (e.g., $C_1$-$C_{30}$ for straight chains, $C_3$-$C_{30}$ for branched chains), 20 or fewer, 12 or fewer, or 7 or fewer. Likewise, in some embodiments cycloalkyls have from 3-10 carbon atoms in their ring structure, e.g. have 5, 6 or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, or from one to six carbon atoms in its backbone structure. Likewise, "lower alkenyl" and "lower alkynyl" have similar chain lengths. Throughout the application, preferred alkyl groups are lower alkyls. In some embodiments, a substituent designated herein as alkyl is a lower alkyl.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Cycloalkyls can be substituted in the same manner.

The term "heteroalkyl", as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "alkylthio" refers to an alkyl group, as defined above, having a sulfur radical attached thereto. In some embodiments, the "alkylthio" moiety is represented by one of —S— alkyl, —S-alkenyl, and —S-alkynyl. Representative alkylthio groups include methylthio, and ethylthio. The term "alkylthio" also encompasses cycloalkyl groups, alkene and cycloalkene groups, and alkyne groups. "Arylthio" refers to aryl or heteroaryl groups. Alkylthio groups can be substituted as defined above for alkyl groups.

The terms "alkenyl" and "alkynyl", refer to unsaturated aliphatic groups analogous in length and possible substitution to the alkyls described above, but that contain at least one double or triple bond respectively.

The terms "alkoxyl" or "alkoxy" as used herein refers to an alkyl group, as defined above, having an oxygen radical attached thereto. Representative alkoxyl groups include methoxy, ethoxy, propyloxy, and tert-butoxy. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. Aroxy can be represented by —O-aryl or O-heteroaryl, wherein aryl and heteroaryl are as defined below. The alkoxy and aroxy groups can be substituted as described above for alkyl.

The terms "amine" and "amino" are art-recognized and refer to both unsubstituted and substituted amines, e.g., a moiety that can be represented by the general formula:

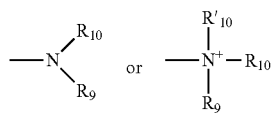

wherein $R_9$, $R_{10}$, and $R'_{10}$ each independently represent a hydrogen, an alkyl, an alkenyl, —$(CH_2)_m$—$R_8$ or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In some embodiments, only one of $R_9$ or $R_{10}$ can be a carbonyl, e.g., $R_9$, $R_{10}$ and the nitrogen together do not form an imide. In still other embodiments, the term "amine" does not encompass amides, e.g., wherein one of $R_9$ and $R_{10}$ represents a carbonyl. In additional embodiments, $R_9$ and $R_{10}$ (and optionally $R'_{10}$) each independently represent a hydrogen, an alkyl or cycloakyl, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of $R_9$ and $R_{10}$ is an alkyl group.

The term "amido" is art-recognized as an amino-substituted carbonyl and includes a moiety that can be represented by the general formula:

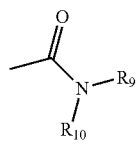

wherein $R_9$ and $R_{10}$ are as defined above.

"Aryl", as used herein, refers to $C_5$-$C_{10}$-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine, pyridazine and pyrimidine, and the like. Those aryl groups having heteroatoms in the ring structure may also be referred to as "aryl heterocycles" or "heteroaromatics". The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN; and combinations thereof.

The term "aryl" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined above for "aryl".

The term "aralkyl", as used herein, refers to an alkyl group substituted with an aryl group (e.g., an aromatic or heteroaromatic group).

The term "carbocycle", as used herein, refers to an aromatic or non-aromatic ring in which each atom of the ring is carbon.

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, ($C_1$-$C_{10}$) alkyl, phenyl or benzyl, and optionally containing 1-3 double bonds and optionally substituted with one or more substituents. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. Heterocyclic groups can optionally be substituted with one or more substituents at one or more positions as defined above for alkyl and aryl, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF3, and —CN.

The term "carbonyl" is art-recognized and includes such moieties as can be represented by the general formula:

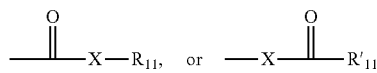

wherein X is a bond or represents an oxygen or a sulfur, and $R_{11}$ represents a hydrogen, an alkyl, a cycloalkyl, an alkenyl, an cycloalkenyl, or an alkynyl, $R'_{11}$ represents a hydrogen, an alkyl, a cycloalkyl, an alkenyl, an cycloalkenyl, or an alkynyl. Where X is an oxygen and $R_{11}$ or $R'_{11}$ is not hydrogen, the formula represents an "ester". Where X is an oxygen and $R_{11}$ is as defined above, the moiety is referred to herein as a carboxyl group, and particularly when $R_{11}$ is a hydrogen, the formula represents a "carboxylic acid". Where X is an oxygen and $R'_{11}$ is hydrogen, the formula represents a "formate". In general, where the oxygen atom of the above formula is replaced by sulfur, the formula represents a "thiocarbonyl" group. Where X is a sulfur and $R_{11}$ or $R'_{11}$ is not hydrogen, the formula represents a "thioester." Where X is a sulfur and $R_{11}$ is hydrogen, the formula represents a "thiocarboxylic acid." Where X is a sulfur and $R'_{11}$ is hydrogen, the formula represents a "thioformate." On the other hand, where X is a bond, and $R_{11}$ is not hydrogen, the above formula represents a "ketone" group. Where X is a bond, and $R_{11}$ is hydrogen, the above formula represents an "aldehyde" group.

The term "monoester" as used herein refers to an analogue of a dicarboxylic acid wherein one of the carboxylic acids is functionalized as an ester and the other carboxylic acid is a free carboxylic acid or salt of a carboxylic acid.

Examples of monoesters include, but are not limited to, to monoesters of succinic acid, glutaric acid, adipic acid, suberic acid, sebacic acid, azelaic acid, oxalic and maleic acid.

The term "heteroatom" as used herein means an atom of any element other than carbon or hydrogen. Examples of heteroatoms are boron, nitrogen, oxygen, phosphorus, sulfur and selenium. Other heteroatoms include silicon and arsenic.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. The heteroatoms such as nitrogen may have hydrogen substituents and/or any permissible substituents of organic compounds described herein which satisfy the valences of the heteroatoms.

In various embodiments, the substituent is selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone, each of which optionally is substituted with one or more suitable substituents. In some embodiments, the substituent is selected from alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone, wherein each of the alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone can be further substituted with one or more suitable substituents.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, thioketone, ester, heterocyclyl, —CN, aryl, aryloxy, perhaloalkoxy, aralkoxy, heteroaryl, heteroaryloxy, heteroarylalkyl, heteroaralkoxy, azido, alkylthio, oxo, acylalkyl, carboxy esters, carboxamido, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, ami nocarboxamidoalkyl, cyano, alkoxyalkyl, perhaloalkyl, arylalkyloxyalkyl, and the like. In some embodiments, the substituent is selected from cyano, halogen, hydroxyl, and nitro.

The term "copolymer" as used herein, generally refers to a single polymeric material that is comprised of two or more different monomers. The copolymer can be of any form, such as random, block, graft, etc. The copolymers can have any end-group, including capped or acid end groups. The term "random copolymer" is used herein in the conventional sense to refer to a polymer containing two or more repeat units that are not in any particular order along the polymer backbone. A random copolymer having repeat units A and B may be represented by the formula:

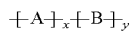

where x and y can be integers representing the number of repeat units of type A and type B, respectively, or x and y can be decimal numbers from 0 to 1 representing the percentage of repeat units of type A and type B, respectively, as will be apparent by the usage.

The term "polypeptoid," as generally used herein, refers to a class of pseudo-peptidic polymers having an aliphatic polyamide backbone with substituents on the backbone nitrogen atoms as opposed to substitution on the backbone carbon centers as in polypeptides. Polypeptoids, while similar in many respects to their polypeptide analogues, do not have stereogenic centers in the backbone like polypeptides. The polypeptoids can lack extensive hydrogen bonding due to the N-substituents. While the backbone chain length of polypeptoids can be long enough to produce tertiary and/or quaternary structure, the tertiary and/or quaternary structure will generally be controlled by the steric and electronic properties of the side chains.

Hydrophobically Modified Polypeptoids

Hydrophobically modified polypeptoids (HMPs) are provided having hydrophobic substituents attached to nitrogen atoms along the backbone. The hydrophobically modified polypeptoids can be chemically synthesized and are not naturally occurring. The hydrophobically modified polypeptoids can be biocompatible. HMPs can have many interesting properties. HMPs at low concentrations can break off parts of liposomes and attach it onto other liposomes. HMPs at higher concentrations can break up liposomes. However they can keep the broken up parts of the liposomes in solution, stabilizing such lipid rafts. The lipid rafts can then be attached onto preexisting liposomes. HMPs can also attach to mucosal surfaces. The HMP can be a poly($\alpha$-peptoid), a poly($\beta$-peptoid), or a poly($\gamma$-peptoid).

Hydrophobically modified polypeptoids can be random copolymers of two, three, four, or more different types of monomers. In various aspects, about 5% to 90%, about 5% to 75%, about 5% to 50%, about 5% to 30%, about 10% to 30%, about 10% to 50%, about 10% to 75%, about 15% to 75%, about 15% to 50%, or about 15% to 30% of the repeat units have a hydrophobic substituent attached to the backbone nitrogen atom. Hydrophobic substituents can include substituted or unsubstituted alkoxy, aryloxy, alkyl, alkenyl, alkynyl, aryl, arylalkyl, carbamate, carboxy, cycloalkyl, ester, ether, haloalkyl, heteroaryl, heterocyclyl, and ketone groups having from 6 to 30 carbon atoms, from 10 to 30 carbon atoms, from 12 to 30 carbon atoms, from 15 to 30 carbon atoms, from 15 to 25 carbon atoms, from 12 to 25 carbon atoms, from 10 to 25 carbon atoms, from 10 to 18 carbon atoms, or from 12 to 18 carbon atoms. In some embodiments, the hydrophobic substituents include lauryl, stearyl, behenyl, and cetyl.

In various aspects, the hydrophobically modified polypeptoid includes one or more monomers that have not been hydrophobically modified. For example, the hydrophobically modified polypeptoid can include a repeat unit having a structure according to any one of Formula A1, Formula A2, and Formula A3

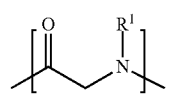

Formula A1

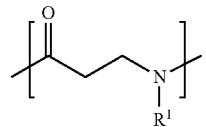

Formula A2

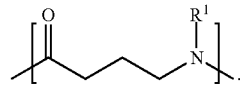

Formula A3

For example, about 20% to 98%, about 30% to 98%, about 30% to 95%, about 40% to 90%, about 40% to 80%, or about 50% to 80% of the repeat units have a structure according to Formula A1, Formula A2, or Formula A3. The substituent $R^1$ can include a hydrogen and substituted and unsubstituted alkoxy, aryloxy, alkyl, alkenyl, alkynyl, aryl, arylalkyl, carbamate, carboxy, cycloalkyl, ester, ether, haloalkyl, heteroaryl, heterocyclyl, and ketone substituents having from 1 to 12 carbon atoms, from 1 to 9 carbon atoms, from 1 to 6 carbon atoms, from 3 to 6 carbon atoms, from 3 to 9 carbon atoms, or from 3 to 12 carbon atoms. In various embodiments, $R^1$ is a methoxyethyl substituent.

The hydrophobically modified polypeptoid includes one or more repeat units that have been hydrophobically modified. For example, the hydrophobically modified polypeptoid can include a repeat unit having a structure according to any one of Formula B1, Formula B2, and Formula B3

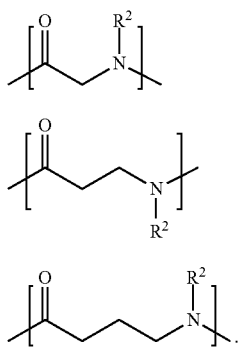

For example, about 2% to 70%, about 2% to 50%, about 5% to 50%, about 5% to 40%, about 5% to 30%, about 5% to 25%, about 10% to 25%, about 10% to 50%, or about 15% to 50% of the repeat units have a structure according to Formula B1, Formula B2, or Formula B3. The substituent $R^2$ can include substituted and unsubstituted alkoxy, aryloxy, alkyl, alkenyl, alkynyl, aryl, arylalkyl, carbamate, carboxy, cycloalkyl, ester, ether, haloalkyl, heteroaryl, heterocyclyl, and ketone groups having from 6 to 30 carbon atoms, from 6 to 25 carbon atoms, from 6 to 20 carbon atoms, from 6 to 18 carbon atoms, from 9 to 18 carbon atoms, from 9 to 20 carbon atoms, from 9 to 25 carbon atoms, from 12 to 25 carbon atoms, from 12 to 20 carbon atoms, or from 12 to 18 carbon atoms. In various embodiments, the $R^2$ substituent is a lauryl, stearyl, behenyl, or cetyl substituent.

The hydrophobically modified polypeptoid can be a random copolymer having a structure according to Formula I or a derivative thereof:

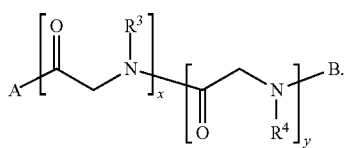

In various aspects, x and y can be integers such that x+y is about 12 to 300, about 15 to 300, about 50 to 300, about 50 to 250, about 50 to 200, about 50 to 150, about 75 to 125, or about 100, e.g. x can be about 40 to 95, about 50 to 95, about 50 to 90, about 50 to 85, about 50 to 80, or about 60 to 75, and y can be about 5 to 50, about 5 to 40, about 5 to 30, about 10 to 30, about 10 to 25, about 15 to 25, about 10 to 25, or about 5 to 25. In various aspects, x and y can be decimal number from 0 to 1 such that x+y is 1.0, wherein x is about 0.2 to 0.98, about 0.5 to 0.98, about 0.5 to 0.95, about 0.5 to 0.9, or about 0.7 to 0.9, and wherein y is about 0.02 to 0.5, about 0.05 to 0.5, about 0.1 to 0.5, about 0.1 to 0.3, about 0.05 to 0.3, or about 0.02 to 0.3. Each occurrence of $R^3$ can be independently selected from hydrogen and substituted and unsubstituted alkoxy, aryloxy, alkyl, alkenyl, alkynyl, aryl, arylalkyl, carbamate, carboxy, cycloalkyl, ester, ether, haloalkyl, heteroaryl, heterocyclyl, and ketone substituents having from 1 to 15 carbon atoms, 1 to 10 carbon atoms, 1 to 6 carbon atoms, 2 to 6 carbon atoms, or 2 to 10 carbon atoms. Each occurrence of $R^4$ can be independently selected from substituted and unsubstituted alkoxy, aryloxy, alkyl, alkenyl, alkynyl, aryl, arylalkyl, carbamate, carboxy, cycloalkyl, ester, ether, haloalkyl, heteroaryl, heterocyclyl, and ketone groups having from 6 to 30 carbon atoms, from 6 to 25 carbon atoms, from 6 to 20 carbon atoms, from 6 to 18 carbon atoms, from 9 to 18 carbon atoms, from 9 to 20 carbon atoms, from 9 to 25 carbon atoms, from 12 to 25 carbon atoms, from 12 to 20 carbon atoms, or from 12 to 18 carbon atoms. In some embodiments, $R^3$ is selected from hydrogen and substituted and unsubstituted alkyl and alkoxy substituents having from 1 to 6 carbon atoms, and $R^4$ is selected from alkoxy, alkyl, and heteroalkyl substituents having from 12 to 18 carbon atoms. For example, $R^3$ can be methoxyethyl and $R^4$ can be lauryl, stearyl, behenyl, or cetyl. A can be selected from the group consisting of substituted and unsubstituted aryl groups, e.g. A can be a substituted or unsubstituted aryl group having about 4 to 20, about 4 to 12, or about 4 to 8 carbon atoms. B can be a hydrogen, or a substituted or unsubstituted alkyl group having about 1 to 30 carbon atoms, about 1 to 12 carbon atoms, or about 1 to 6 carbon atoms.

The hydrophobically modified polypeptoid can be a random copolymer having a structure according to Formula II or a derivative thereof:

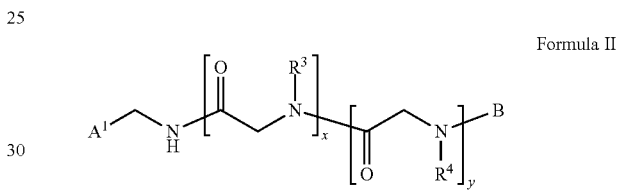

where x, y, $R^3$, and $R^4$, and B are as described above, and where $A^1$ is a substituted or unsubstituted aryl group having about 4 to 20, about 4 to 12, or about 4 to 8 carbon atoms. For example, $A^1$ can be a substituted or unsubstituted phenyl group.

The hydrophobically modified polypeptoid can include any number of repeat units, e.g. about 10 to 500, about 10 to 400, about 12 to 400, about 12 to 300, about 50 to 400, about 50 to 300, about 50 to 200, about 75 to 200, about 75 to 150, about 75 to 125, or about 100. The hydrophobically modified polypeptoid can have a molecular weight from about 10 kDa to 30 kDa, about 10 kDa to 20 kDa, about 12 kDa to 20 kDa, about 12 kDa to 18 kDa, or about 14 kDa.

Methods of Making Hydrophobically Modified Polypeptoids

Various methods of making hydrophobically modified polypeptoids are provided herein. The methods can include polymerizing a quantity of two or more different N-substituted N-carboxyanhydride monomers at an elevated temperature to produce the hydrophobically modified polypeptoid, wherein one or more of the repeat units comprise a nitrogen atom in the backbone having a hydrophobic substituent attached thereto. The methods can include ring opening polymerization of two or more different N-substituted heterocycles such as N-substituted N-carboxyanhydride monomers. The polymerization can proceed in the presence of suitable nucleophilic initiators such as primary amines. For example, in some aspects the primary amine can have the structure $A^1$-$CH_2$—$NH_2$, where $A^1$ is as described above. The polymerization can be performed at an elevated temperature, e.g. about 32° C. to 70° C., about 40° C. to 70° C. about 40° C. to 60° C., or about 45° C. to 60° C.

In various aspects, the monomers include different N-substituted N-carboxyanhydride monomers with hydrophobic substituents on the N, e.g. having a structure according to Formula III or a derivative thereof

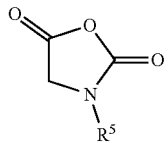

Formula III wherein $R^5$ can be selected from substituted and unsubstituted alkoxy, aryloxy, alkyl, alkenyl, alkynyl, aryl, arylalkyl, carbamate, carboxy, cycloalkyl, ester, ether, haloalkyl, heteroaryl, heterocyclyl, and ketone groups having from 6 to 30 carbon atoms, from 6 to 25 carbon atoms, from 6 to 20 carbon atoms, from 6 to 18 carbon atoms, from 9 to 18 carbon atoms, from 9 to 20 carbon atoms, from 9 to 25 carbon atoms, from 12 to 25 carbon atoms, from 12 to 20 carbon atoms, or from 12 to 18 carbon atoms. In some aspects, $R^5$ can be lauryl, stearyl, behenyl, or cetyl.

In various aspects, the monomers include those having a structure according to Formula IV or a derivative thereof

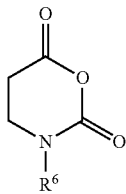

Formula IV wherein $R^6$ can be selected from substituted and unsubstituted alkoxy, aryloxy, alkyl, alkenyl, alkynyl, aryl, arylalkyl, carbamate, carboxy, cycloalkyl, ester, ether, haloalkyl, heteroaryl, heterocyclyl, and ketone groups having from 6 to 30 carbon atoms, from 6 to 25 carbon atoms, from 6 to 20 carbon atoms, from 6 to 18 carbon atoms, from 9 to 18 carbon atoms, from 9 to 20 carbon atoms, from 9 to 25 carbon atoms, from 12 to 25 carbon atoms, from 12 to 20 carbon atoms, or from 12 to 18 carbon atoms. In some aspects, $R^6$ can be lauryl, stearyl, behenyl, or cetyl.

In various aspects, the monomers include those having a structure according to Formula V or a derivative thereof

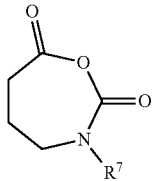

Formula V wherein $R^7$ can be selected from substituted and unsubstituted alkoxy, aryloxy, alkyl, alkenyl, alkynyl, aryl, arylalkyl, carbamate, carboxy, cycloalkyl, ester, ether, haloalkyl, heteroaryl, heterocyclyl, and ketone groups having from 6 to 30 carbon atoms, from 6 to 25 carbon atoms, from 6 to 20 carbon atoms, from 6 to 18 carbon atoms, from 9 to 18 carbon atoms, from 9 to 20 carbon atoms, from 9 to 25 carbon atoms, from 12 to 25 carbon atoms, from 12 to 20 carbon atoms, or from 12 to 18 carbon atoms. In some aspects, $R^7$ can be lauryl, stearyl, behenyl, or cetyl.

Uses of Hydrophobically Modified Polypeptoids

The HMPs can be used to develop antimicrobial coatings since they disrupt cell membranes in analogy with the disruption of liposomes. Antimicrobial compositions can include one or more HMPs in a suitable carrier, optionally including one or more additional antimicrobial agents.

The HMPs can be used to deliver drug components encapsulated in lipid rafts. This is especially valid for cancer therapeutics since several cancer drugs are water insoluble but soluble in lipids. Lipid raft can include a plurality of the HMPs self-assembled into a lipid raft, optionally including one or more additional lipids. The lipid rafts can include one or more hydrophobic drugs incorporated into the HMPs of the lipid raft.

HMPs can be used to prepare particles, e.g. nanoparticles and microparticles. In various aspects, the particle can include a liposome having a lipid bilayer forming an interior region and an exterior surface, a hydrophilic drug in the interior region, and a plurality of hydrophobically modified polypeptoids on the exterior surface of the liposome. The liposome can be unilamellar or multilamellar. The hydrophobically modified polypeptoids on the surface of the liposome can encapsulate a hydrophobic drug. The particles can have a diameter of about 50 nm to 5 microns, about 50 nm to 1 micron, about 50 nm to 500 nm, about 50 nm to 250 nm, or about 70 nm to 125 nm.

Examples of hydrophobic drugs include, but are not limited to, ROCK inhibitors, SYK-specific inhibitors, JAK-specific inhibitors, SYK/JAK or multi-Kinase inhibitors, MTORs, STAT3 inhibitors, VEGFR/PDGFR inhibitors, c-Met inhibitors, ALK inhibitors, mTOR inhibitors, PI3Kδ inhibitors, PI3K/mTOR inhibitors, p38/MAPK inhibitors, NSAIDs, steroids, antibiotics, antivirals, antifungals, antiparsitic agents, blood pressure lowering agents, cancer drugs or anti-neoplastic agents, immunomodulatory drugs, psychiatric medications, dermatologic drugs, lipid lowering agents, anti-depressants, anti-diabetics, anti-epileptics, anti-gout agents, anti-hypertensive agents, anti-malarials, anti-migraine agents, anti-muscarinic agents, anti-thyroid agents, anxiolytic, sedatives, hypnotics, neuroleptics, β-blockers, cardiac inotropic agents, corticosteroids, diuretics, antiparkinsonian agents, gastro-intestinal agents, histamine H-receptor antagonists, lipid regulating agents, nitrates and other antianginal agents, nutritional agents, opioid analgesics, sex hormones, and stimulants.

The HMPs described herein can be used, not just in pharmaceutical applications, but in applications related to food packaging (antimicrobial) and cosmetics and consumer products. For example, is some aspects an antimicrobial food packaging can include one or more HMPs described herein.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

The examples below demonstrate that introduction of decyl groups to a hydrophilic polypeptoid backbone induced interaction between the modified polypeptoid and liposomes through the insertion of hydrophobes into the lipid bilayer. This lead to a breakdown of the liposome structural integrity and a gradual solubilization of the liposome into mixed aggregates of lipids and the modified polypeptoid. The HMP polymeric amphiphile was able to attach fragments onto existing and surviving liposomes to create additional layers on the surface of liposomes. The polymer chain served as the connecting material between lipid containing fragments and liposomal bilayers allowing a buildup of bilayers on the surface of a liposome.

The potential to build bilayers onto liposomes using a designed connective polymeric amphiphile has significant technical implications. These concepts can be used for the attachment of drug-containing lipid entities to cell membranes and to vesicle systems, including multiple bilayers containing liposomes with multiple drug components in each.

Materials.

L-α-phosphatidylcholine (PC) was purchased from Avanti Polar Lipids. Deuterium oxide was purchased from Cambridge Isotope Laboratories. Deionized (DI) water generated by ELGA reverse osmosis water purification system (MEDICA 15BP) with a resistance of 18.2 MΩ·cm was used in all experiments. All chemicals were used as received unless otherwise noted. All the solvents used in polymerization were purified by passing through alumina columns under argon.

Example 1: Synthesis of poly[(N-methoxyethyl glycine)-r-(N-decyl glycine)] P(NMeOEtG-r-NDG)

The polymer was synthesized by benzyl amine-initiated ring-opening polymerization of the corresponding N-substituted N-carboxyanhydride monomers (MeOEt-NCA and De-NCA). The reaction scheme is depicted in FIG. 1, and the detailed procedure is described below. The unmodified polypeptoid (UMP), poly(N-methoxyethyl glycine) (PNMeOEtG), was synthesized by polymerization of N-methoxyethyl NCA, whereas the hydrophobically modified polypeptoid (HMP), poly[(N-methoxyethyl glycine)-r-(N-decyl glycine)] (P(NMeOEtG-r-NDG)), was synthesized by copolymerization of N-methoxyethyl NCA and N-decyl NCA. Both UMP and HMP were designed to reach polymerization degree of 100. In a typical synthesis of HMP, stock solutions of N-methoxyethyl NCA and N-decyl NCA in THF were mixed in a small vial. Benzyl-NH$_2$/THF stock solution was added to the above mixture and heated at about 50° C. for 48 h. Aliquots were taken and analyzed by $^1$H NMR spectroscopy to check conversion. The polymer was precipitated out by adding excess hexanes, collected by filtration, and dried under vacuum to obtain the final product as a white solid.

Synthesis of PNMeOEtG$_{74}$-r-PNDG$_{26}$

Figure 2A:
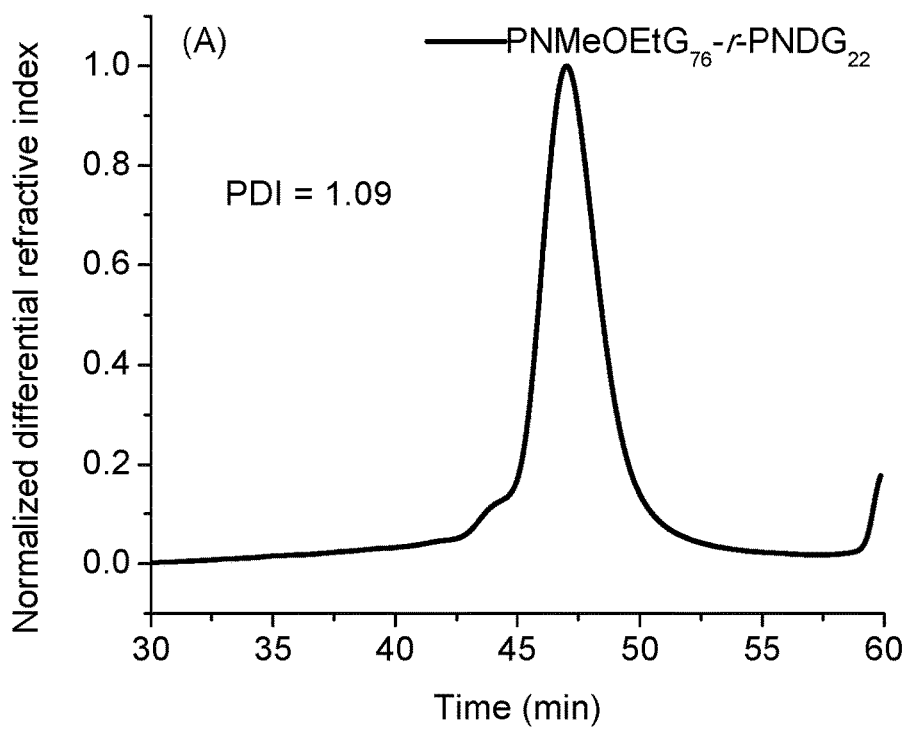
FIGS. 2A-2C depict size exclusion chromatography with differential refractometer (SEC-DRI) chromatograms of (FIG. 2A) PNMeOEtG$_{74}$-r-PNDG$_{26}$, (FIG. 2B) PNMeOEtG$_{89}$-r-PNDG$_{9}$, and (FIG. 2C) PNMeOEtG$_{106}$ using polystyrene as the standard in LiBr/DMF (0.1M).

Inside the glovebox, stock solutions of MeOEt-NCA (1.3 mL, 0.4 M, 0.52 mmol) and De-NCA (0.3 mL, 0.4 M, 0.13 mmol) in THF were mixed into a small vial. A known volume of BnNH$_2$/THF stock solution (70 µL, 6.5 µmol, 92.7 mM) was added to the above mixture and heated at 50° C. for 48 h. Aliquots were taken and analyzed by FT-IR spectroscopy to check conversion. The polymer was precipitated out by adding excess hexanes. The polymer was collected by filtration and dried under vacuum to obtain the final product as a white solid (73.2 mg, 85.1% yield). The structure was confirmed by $^1$H NMR and by size exclusion chromatography (FIG. 2A).

Synthesis of PNMeOEtG$_{89}$-r-PNDG$_9$

Figure 2B:
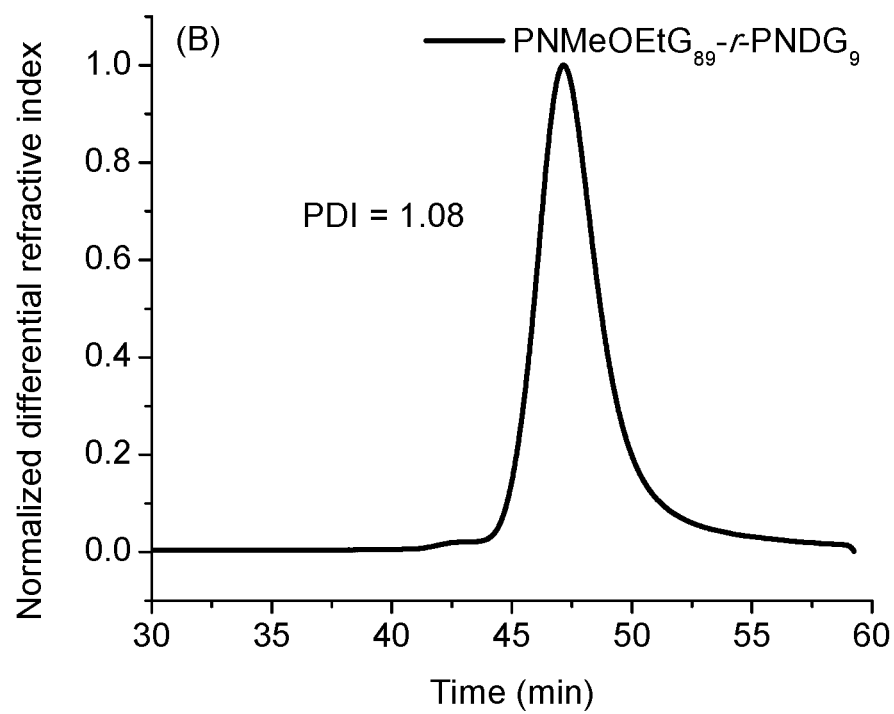

Inside the glovebox, stock solutions of MeOEt-NCA (1.3 mL, 0.4 M, 0.52 mmol) and De-NCA (0.13 mL, 0.4 M, 0.052 mmol) in THF were mixed into a small vial. A known volume of BnNH$_2$/THF stock solution (62.3 µL, 5.8 µmol, 92.7 mM) was added to the above mixture and heated at 50° C. for 48 h. Aliquots were taken and analyzed by FT-IR spectroscopy to check conversion. The polymer was precipitated out by adding excess hexanes. The polymer was collected by filtration and dried under vacuum to obtain the final product as a white solid (61.6 mg, 88.2% yield). The structure was confirmed by $^1$H NMR and by size exclusion chromatography (FIG. 2B).

Synthesis of PNMeOEtG$_{100}$

Figure 2C:
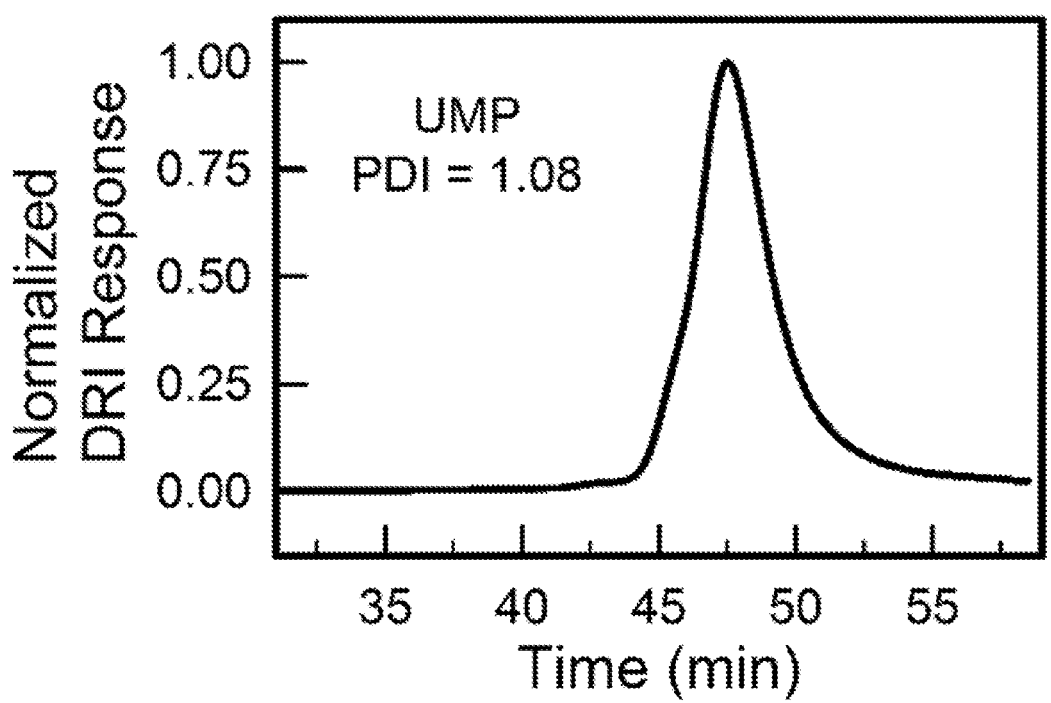

Inside the glovebox, stock solutions of MeOEt-NCA (1.3 mL, 0.4 M, 0.52 mmol) in THF were mixed in a small vial with a known volume of BnNH$_2$/THF stock solution (70 µL, 6.5 µmol, 92.7 mM) was added to the above mixture and heated at 50° C. for 48 h. Aliquots were taken and analyzed by FT-IR spectroscopy to check conversion. The polymer was precipitated out by adding excess hexanes. The polymer was collected by filtration and dried under vacuum to obtain the final product as a white solid (82.3-87.8% yield). The structure was confirmed by $^1$H NMR and by size exclusion chromatography (FIG. 2C).

NMR and Size Exclusion Chromatography (SEC) Analysis of the Polypeptoids.

$^1$H NMR spectra were obtained on Bruker AV-400 spectrometers at 298 K. Chemical shifts (δ) given in parts per million (ppm) were calibrated to proton impurities of CD$_2$Cl$_2$ or D$_2$O. SEC analysis of the polypeptoids were performed using an Agilent 1200 system (Agilent 1200 series degasser, isocratic pump, autosampler and column heater) equipped with three Phenomenex 5 µm, 300×7.8 mm columns [100 Å, 1000 Å and Linear (2)], a Wyatt OptilabrEX differential refractive index (DRI) detector with a 690 nm light source, and a Wyatt DAWN EOS multiangle light scattering (MALS) detector (GaAs 30 mW laser at λ=690 nm). DMF with 0.1M LiBr was used as the eluent at a flow rate of 0.5 mL·min$^{-1}$. The column and detector temperature was set at 25° C. All data analysis was performed using Wyatt Astra V 5.3 software. The polydispersity index (PDI) were obtained by conventional SEC analysis with a calibration curve. The calibration curve was constructed from twenty three pauci-disperse polystyrene standards (M$_n$=590 g·mol$^{-1}$-1472 kg·mol$^{-1}$, Polymer Laboratories, Inc.) using Astra's column calibration template. Relative PDI was then calculated using Astra's conventional calibration template. The sample for SEC analysis was prepared as below: 130 µl reaction mixture of HMP (or UMP) was added to 1 ml of DMF with 0.1 M LiBr and mixed thoroughly. This mixture was directly injected into SEC instrument for analysis.

Cytotoxicity Study.

The cytotoxicity study was conducted by adapting a reported procedure (Xuan, et al, "Synthesis and In Vitro Studies of a Series of Carborane-containing Boron Dipyrromethanes (BODIPYs). (*J. Med. Chem.* 2016, 59, 2109-2117.) The HEp2 cells were plated at 7500 cells per well in a Costar 96-well plate (BD biosciences) and allowed to grow for 48 h. The stock solution of polymer in medium (2 mg/mL) was diluted into final working concentrations (0, 0.0625, 0.125, 0.25, 0.5, and 1 mg/mL). The cells were exposed to the working solutions of polymer up to 1 mg/mL and incubated overnight (37° C., 95% humidity, 5% CO$_2$).

Figure 3:
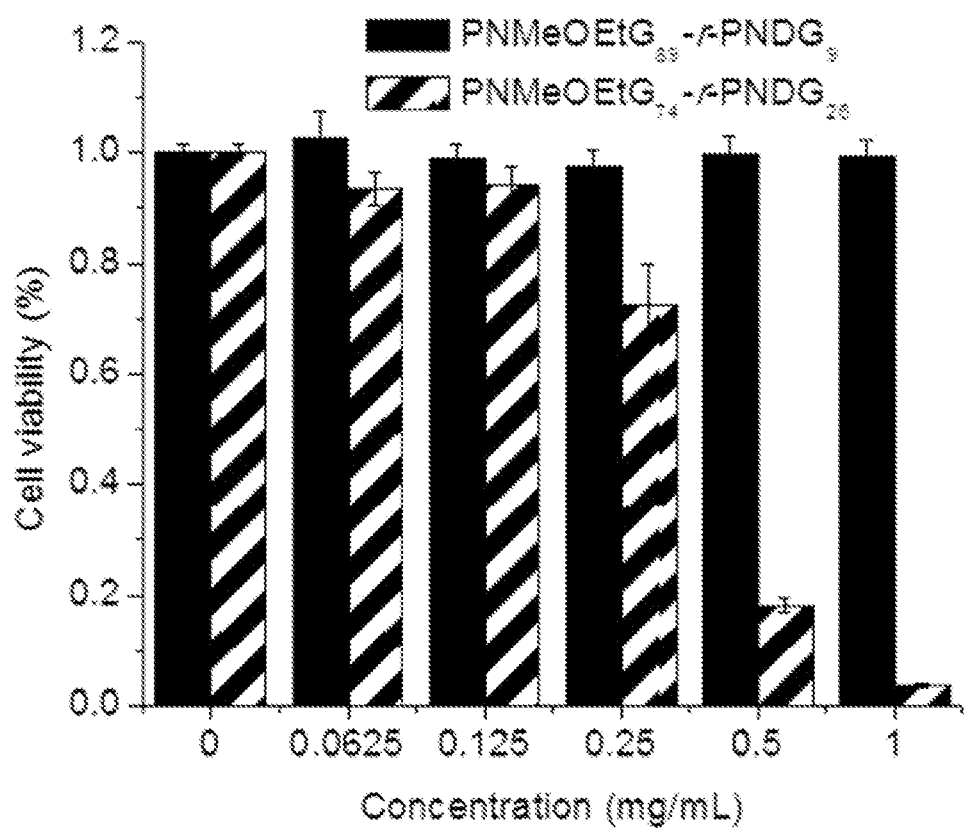
FIG. 3 Cytotoxicity study of PNMeOEtG$_{74}$-r-PNDG$_{26}$ and PNMeOEtG$_{89}$-r-PNDG$_{9}$.

The polymer solution was removed, and the cells were washed with 1×PBS. The medium containing 20% CellTiter Blue (Promega) was added and incubated for 4 h. The viability of cells is measured by reading the fluorescence of the medium at 570/615 nm using a BMG FLUOstar Optima micro-plate reader. The fluorescence signal of viable (untreated) cells was normalized to 100%. The cell viability is plotted as a function of the polymer concentration in FIG. 3.

Polypeptoid Characterization through $^1$H NMR and Size Exclusion Chromatography (SEC).

The compositions of UMP and HMP were determined by $^1$H NMR spectroscopy. The number average degree of polymerization (DP) of UMP was determined by the integration of methylene group in the backbone at 4.52, 4.41, 4.18, 4.10 ppm relative to the integration of benzyl end-group at 7.24 and 7.31 ppm. The DP of HMP was determined by the integration of methyl group in the side chain and the integration of methylene groups in the backbone relative to the integration of benzyl end-group at 7.24 and 7.31 ppm. The integrations give UMP a DP of 106 and HMP a DP of around 98 containing 10 mol % N-decyl glycine units and a DP of around 100 containing 26 mol % N-decyl glycine units. The corresponding molecular weight of $PNMeOEtG_{100}$ is about 12509 g/mol, and the corresponding molecular weight of $PNMeOEtG_{74}$-r-$PNDG_{26}$ is about 13939 g/mol. The size exclusion chromatographic (SEC) analysis indicated the monomodal and narrow distribution of polymer molecular weight for both UMP and HMP (FIGS. 2A-2C), with low PDI of 1.09 and 1.08, respectively.

Example 2: Polypeptoid Interactions with Lipid Bilayers

UMP and the HMP $PNMeOEtG_{74}$-r-$PNDG_{26}$ were prepared as described in Example 1. For Example 2, unless indicated otherwise, HMP refers to the HMP from Example 1 $PNMeOEtG_{74}$-r-$PNDG_{26}$ having a degree of polymerization of about 100 and containing 26 mol % N-decyl glycine units. As the first step to the characterization of the interactions between the polymers and liposomes, SANS experiments were performed on the individual systems. The results were compared to control sample solutions containing liposomes with varying amounts of UMP as well as to sample solutions containing liposomes and varying amounts of the HMP.

Liposome Preparation.

L-α-phosphatidylcholine (PC) liposomes were prepared using thin film hydration method. (Holder, G. E.; et al., *J. Neuroimmune Pharmacol.* 2014, 9, 716-726). 0.1 g PC was first dissolved in a round bottom flask by 15 ml mixed solution of chloroform and methanol at a volume ratio of 2:1. The solvent was then evaporated using a rotary evaporator (Buchi R-205) at room temperature under 100 mbar for 3 hours to form a thin lipid film. The pressure was further reduced to 6 mbar for 30 min to remove solvent residual. The obtained thin lipid film was hydrated with DI water at 50° C. The aqueous suspension was transferred to a syringe and extruded 21 times through a 100 nm polycarbonate membrane to acquire liposomes with an average diameter of 100 nm.

Preparation of Liposome and Polypeptoid Mixtures.

DI water was used to dilute the liposome stock suspension to 0.5%. HMP solutions at concentrations of 0.25%, 0.5%, 0.75% and 1% were mixed with a 0.5% liposome suspension at 1:1 volume ratio, respectively, to acquire solutions with the liposome concentration fixed at 0.25% and varying concentrations of HMP. The resulting mixtures were labeled as LIP0125HMP, LIP025HMP, LIP0375HMP and LIP05HMP denoting the final overall concentrations of HMP. Liposomes were also incubated with UMP at overall concentrations of 0.25% and 0.5% as negative controls, denoted as LIP025UMP and LIP05UMP, respectively. The liposome solution with the overall concentration of 0.25% was used as the blank control, denoted as LIP. Essentially all samples had the same concentration of lipid (0.25%) and the studies were done with varying concentrations of polymers. All samples were incubated for at least 12 hours prior to instrumental characterization. All concentrations are reported as wt %.

SANS Data Collection and Reduction.

The SANS experiments were carried out on the extended-Q range small angle neutron scattering (EQ-SANS) diffractometer at the Spallation Neutron Source (SNS) at the Oak Ridge National Laboratory (ORNL). All samples were prepared with pure deuterium oxide to generate sufficient scattering contrast. The samples were loaded into 2 mm path-length quartz banjo cells (Hellma, Germany) and placed in a 42-position sample chamber. Measurements were taken at room temperature (20° C.). The instrument was operated in a 60 Hz mode with a neutron wavelength (λ) range of 2.5 Å-6.1 Å. The sample-to-detector distance was set to 4 m. This configuration provides an effective q-range of 0.009 Å$^{-1}$-0.44 Å$^{-1}$. The scattering vector, q, is defined by $q=4\pi[\sin(\theta/2)]/\lambda$ where θ is the scattering angle.

The reduction of SANS data was performed using MantidPlot software following standard procedures (Liu, Y. et al., *Biochim. Biophys. Acta, Biomembr,* 2014, 1838, 1871-1880). The data were corrected for instrument dark current, detector sensitivity, incident beam normalization, sample transmission and solvent background. A calibrated standard provided by ORNL, Porasil B, was used to obtain the scale factor which was used to convert the data into absolute intensity units (cm$^{-1}$). Reduced data were azimuthally averaged using MantidPlot to generate scattering intensity per unit volume, I(q), as a function of q.

Cryo-TEM Imaging.

Cryo-TEM imaging was done on an FEI G2 F30 Tecnai TEM operated at 150 kV. To prepare the sample, a 300-mesh lacey carbon grid (Electron Microscopy Sciences) was picked up by a tweezer and mounted on the plunging station of an FEI Vitrobot. 10 μl of the solution was applied to the grid. The excess liquid was blotted by filter paper attached to arms of the Vitrobot for 2 seconds to form a thin film. The sample was then vitrified by plunging into liquid ethane. The vitrified sample was finally transferred onto a single tilt cryo specimen holder for imaging.

Small Angle Neutron Scattering (SANS) Results

Figure 4A:
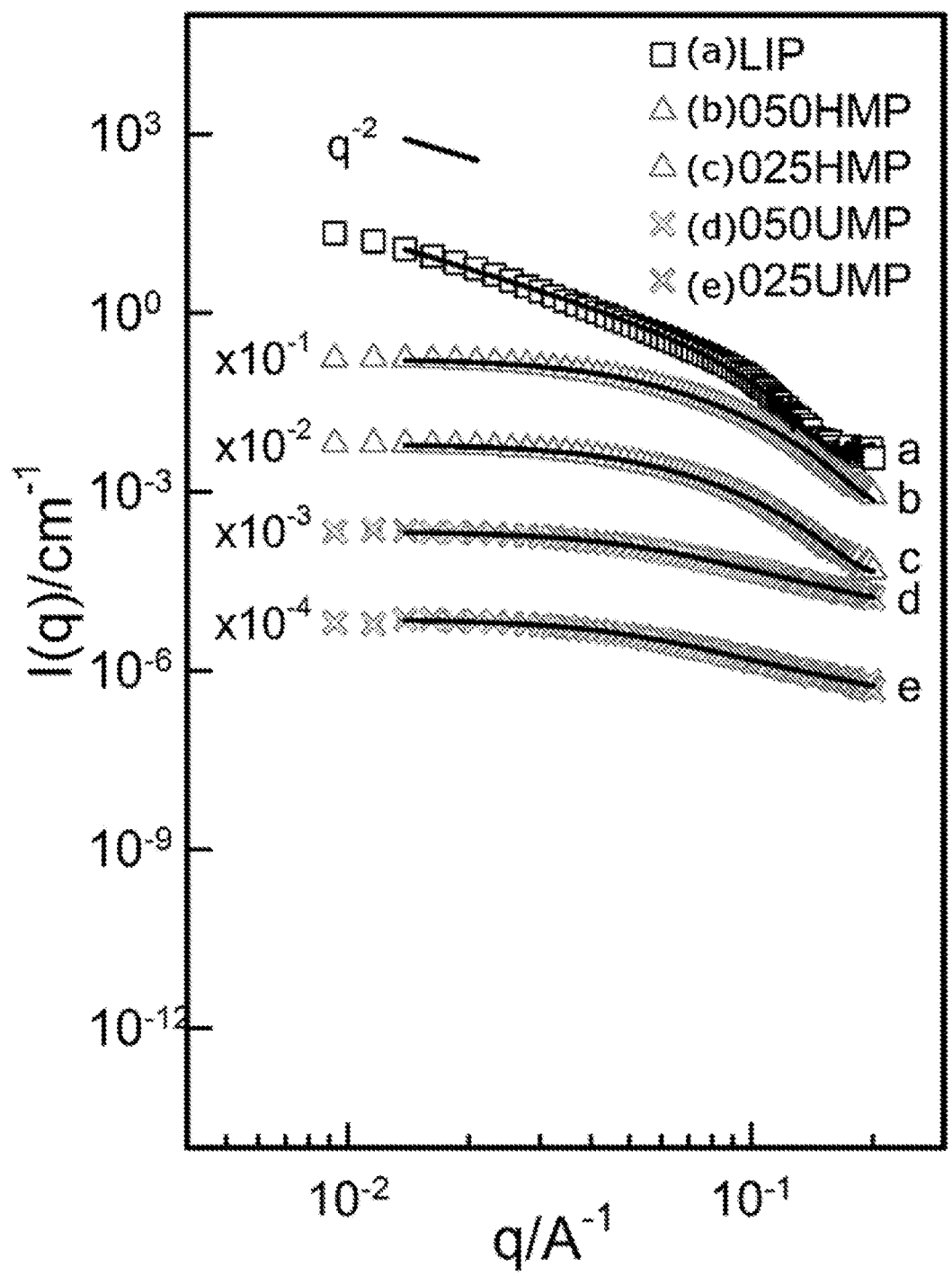
FIG. 4A shows the scattering profiles of 0.25% liposome (LIP, a), 0.5% HMP (050HMP, b), 0.25% HMP (025HMP, c), 0.5% UMP (050UMP, d) and 0.25% UMP (025UMP, e) in D$_2$O. The curves are scaled and separated by a factor of 0.1. The solid lines are best-fit results to the corresponding models.
Figure 4B:
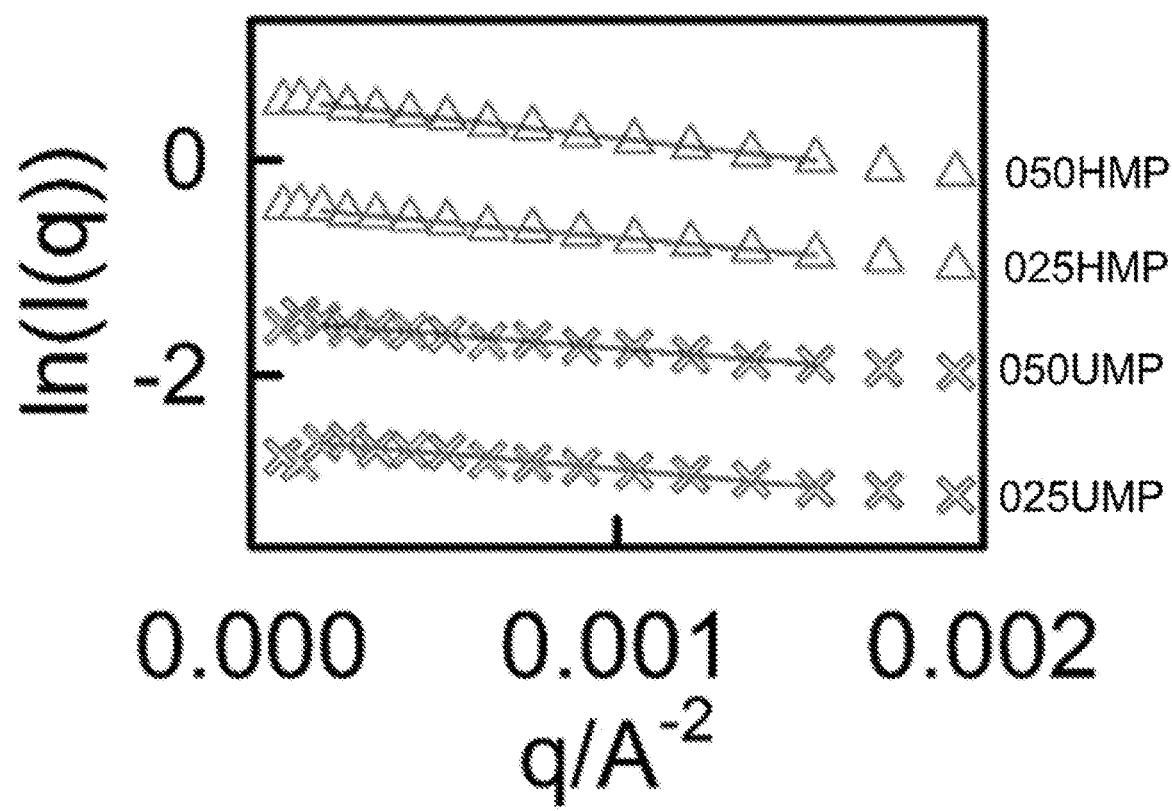
FIG. 4B shows the corresponding Guinier plots (ln(I) vs. q$^2$) of the HMP and UMP samples.

As the first step to the characterization of the interactions between the polymers and liposomes, SANS experiments were carried out on the individual systems with the results shown in FIGS. 4A-4B. As shown here, the data are separated by a scale factor of 0.1 for clarity and ease in visualization especially at the larger q values. The scattering intensity, I(q), is determined by the structure factor, S(q), and the form factor, P(q). In dilute, noninteracting system, S(q) is close to 1. Therefore, I(q) is determined by P(q).

Curve a in FIG. 4A shows the scattering profile of 0.25% liposome suspension (LIP). For a detailed analysis of the form factor, the scattering data was fitted to the PolyCore-MultiShell model developed by the National Institute of Standards and Technology (NIST) using IgorPro software. When N (model parameter, number of shells) is fixed at 1, P(q) can be described as $$P(q) = \frac{\text{scale}}{V_{shell}}\left[\frac{3V_1(\rho_1-\rho_2)J_1(qR_1)}{qR_1} + \frac{3V_2(\rho_2-\rho_{solv})J_1(qR_2)}{qR_2}\right]^2 + bkg \quad (1)$$

where scale is a scale factor, $V_{shell}$ is the volume of the shell, $V_1$ is the volume of the core, $V_2$ is the total volume, $R_1$ is the radius of the core, $R_2$ is the outer radius of the shell, $\rho_1$ is the scattering length density of the core, $\rho_2$ is the scattering length density of the shell, $\rho_{solv}$ is the scattering length density of the solvent, bkg is the background level, and $J_1(x) = (\sin x - x \cos x)/x^2$. With polydispersity in the core radius being considered, the form factor is averaged over the Schultz distribution (Lee, et al., *Langmuir* 2005, 21, 26-33.)

$$P(q) = \int f(R)P(q, R)\,dR \quad (2)$$

$$f(R) = \left(\frac{z+1}{R_0}\right)^{z+1}\frac{R^z}{\Gamma(z+1)}\exp\left[-(z+1)\frac{R}{R_0}\right] \quad (3)$$

where $f$ is the distribution function, R is the core radius, $R_0$ is the average core radius, $\Gamma(x)$ is the gamma function, and z is the polydispersity index. The polydispersity, p, is related to z through $$p = \frac{1}{\sqrt{z+1}} \quad (4)$$

The scattering profile of the liposome system (FIG. 4A, curve a) indicates a $q^{-2}$ dependence in the decay at low q range, which is characteristic of non-interacting liposomes (Pabst, G.; Kučerka, et al., Liposomes, Lipid Bilayers and Model Membranes: From Basic Research to Application; CRC Press: Boca Raton, 2014.). The solid line shows the best-fit of the scattering data of liposome. The fitting results show a liposome diameter of 99.4 nm with a polydispersity of 0.17. The shell thickness, or the lipid bilayer thickness, is 3.68 nm, which is close to the reported value in the literature.

The scattering curves for HMP samples were found to be best fitted to the Flexible Cylinder model (Pedersen, J. S.; Schurtenberger, P., *Macromolecules* 1996, 29, 7602-7612). For UMP, the curve was also fitted by the Gaussian Coil model, but the excellent fit of the Flexible Cylinder model was retained to provide a direct comparison of parameters with HMP. In both cases it was assumed that the contour length L» the Kuhn length b. The results are presented in FIG. 4A as solid black lines. L was calculated based on polymerization degree and was fixed in the Flexible Cylinder model calculations to estimate b and the axial radius of the polymer aggregates, $R_{cyl}$. The radius of gyration, $R_g$, of each sample was also calculated from the model fit results (Pedersen, J. S.; Schurtenberger, P., *Macromolecules* 1996, 29, 7602-7612). The results are included in Table 1.

TABLE 1

Model Fitting Parameters for SANS Data

| Sample | Component | | $R_{cyl}{}^a$ (nm) | $L^b$ (nm) | $b^c$ (nm) | $R_g$ (Model$^d$) | $R_g$ (Guinier) |
|---|---|---|---|---|---|---|---|
| 025HMP | — | 0.25% HMP | 1.7 | 38.0 | 0.76 | 2.6 | 3.0 |
| 050HMP | — | 0.5% HMP | 1.7 | 38.0 | 1.08 | 3.0 | 3.4 |
| 025UMP | — | 0.25% UMP | 0.6 | 39.4 | 1.00 | 3.0 | 3.0 |
| 050UMP | — | 0.5% UMP | 0.6 | 39.4 | 0.87 | 2.8 | 2.9 |
| LIP050HMP | 0.25% liposome | 0.5% HMP | 2.0 | 38.0 | 3.43 | 5.0 | 4.7 |

$^a R_{cyl}$: cylinder radius;
$^b$L: contour length;
$^c$b: Kuhn length;
$^d R_g$ values calculated based on fitting results of Flexible Cylinder model.

FIG. 4B shows the empirical Guinier plots where data in the range of $0.00014\ \text{Å}^{-2} < q^2 < 0.0016\ \text{Å}^{-2}$ were used in the calculation for $R_g$. The results of the Guinier analysis are listed in Table 1 and show very reasonable agreement with the $R_g$ values calculated from the model fitting results. To summarize Table 1, the values of $R_g$ between UMP and HMP show insignificant differences at both concentrations suggesting that the state of the polymers over this range of concentration remains essentially the same. The fact that the form factor fits the low q range in these dilute systems shows that there is minimal intermolecular aggregation. As shown in subsequent discussion, significant changes in $R_g$ values are obtained through the interaction of HMP with lipid bilayers.

Figure 5:
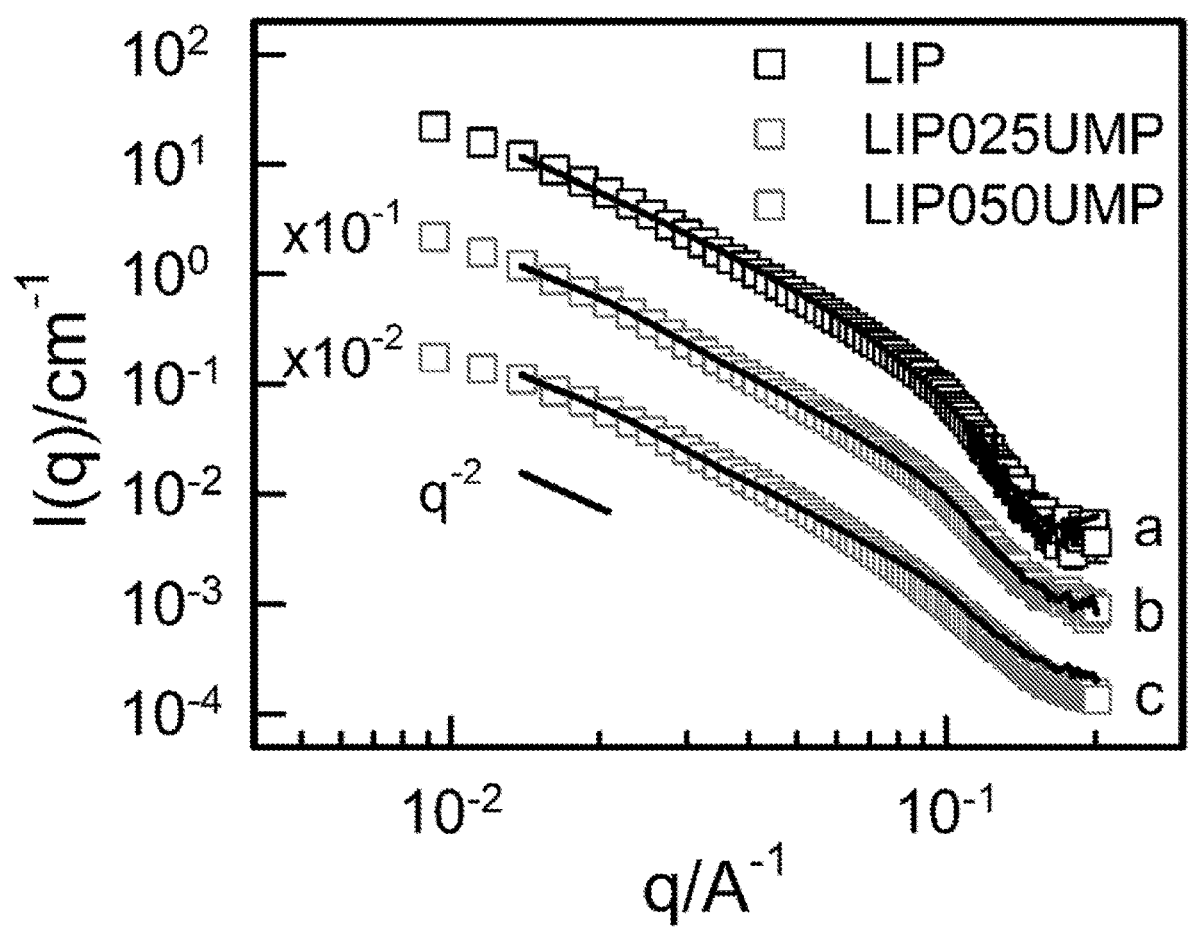
FIG. 5 is a graph of the scattering profiles of 0.25% liposomes incubated with 0% UMP (LIP, a), 0.25% UMP (LIP025UMP, b) and 0.5% UMP (LIP050UMP, c). The scattering curves are separated by a scale factor of 0.1 for clarity. Addition of UMP has little effect on the scattering pattern which is essentially a linear summation of the scattering data of the individual components.

To explore the interactions between liposomes and polypeptoids, solutions were prepared containing 0.25% liposomes with 0.25% and 0.5% UMP as control samples. The SANS data for these samples (LIP025UMP and LIP050UMP, respectively) are shown in FIG. 5. At low q, the slope of the scattering curve remains −2 when liposomes are mixed with UMPs, which is indicative that the bilayer structure is maintained when liposome is incubated with UMPs. We note that the scattering intensity of the mixtures is essentially just the concentration weighted summation of the individual components with the scattering from the liposomes dominating the pattern at low q. These observations show that there is no structural change in the system induced by UMP and that UMP and liposomes exist as independent entities in solution.

Figure 6A:
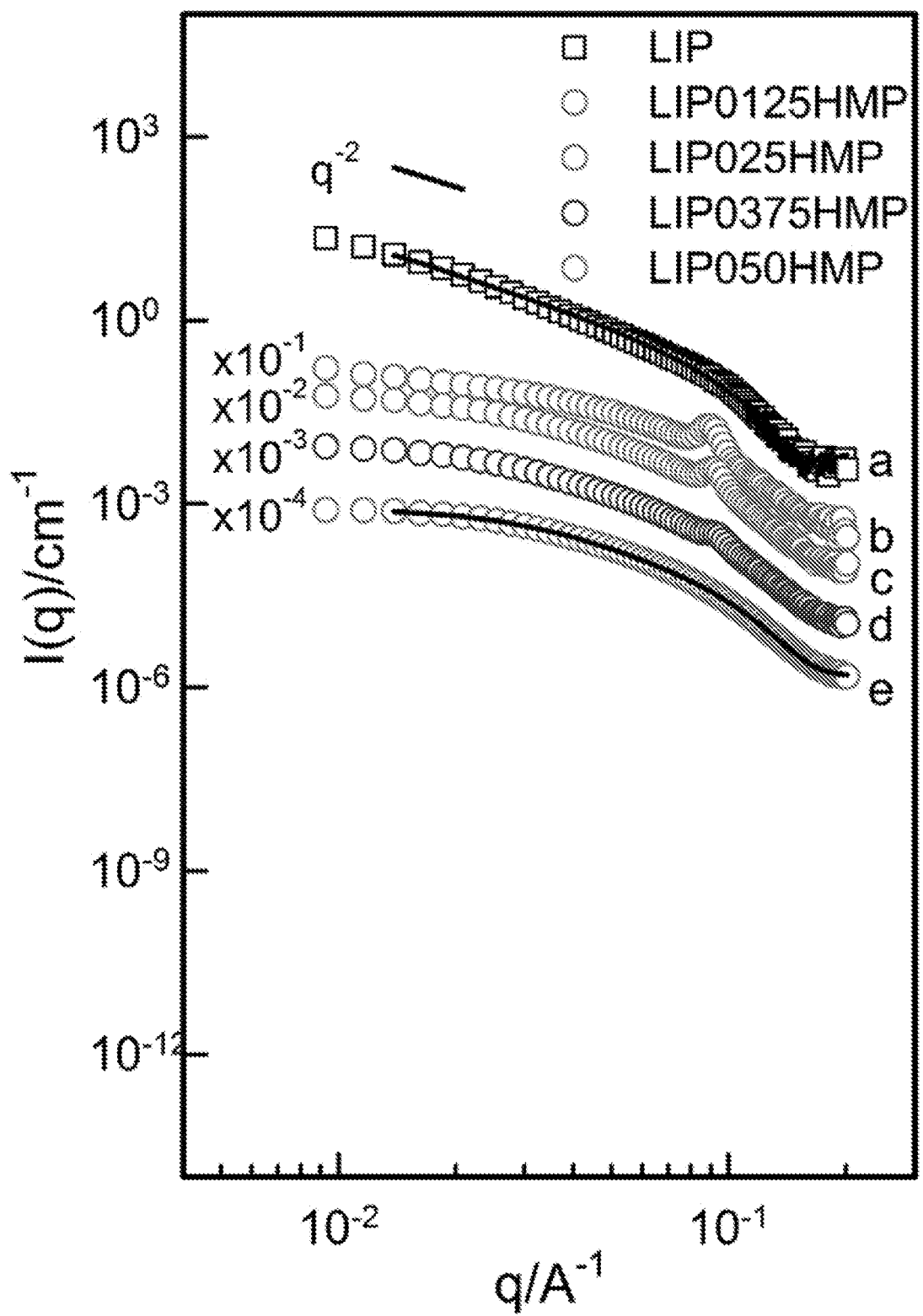
FIG. 6A depicts the SANS data of 0.25% liposomes incubated with 0% HMP (LIP, a), 0.125% HMP (LIP0125HMP, b), 0.25% HMP (LIP025HMP, c), 0.375% HMP (LIP0375HMP, d) and 0.5% HMP (LIP050HMP, e). The scattering curves are separated by a scale factor of 0.1 for clarity. The black solid lines show best-fit results to the corresponding models.
Figure 6B:
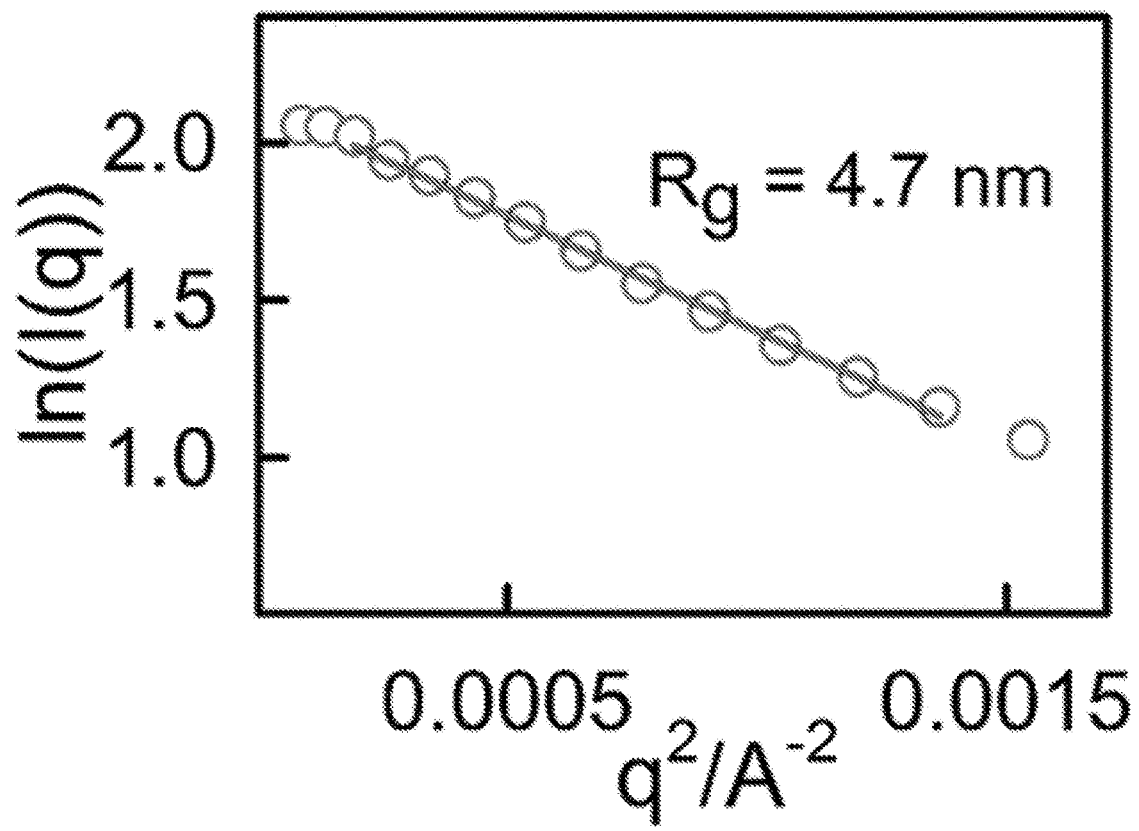
FIG. 6B shows the corresponding Guinier plot of the scattering data of LIP0125HMP giving an $R_g$ of 4.7 nm.

FIGS. 6A-6B illustrates the scattering patterns of mixtures of liposomes and HMP, and it is immediately clear that there are significant changes in the patterns in comparison to the scattering from LIP. With the addition of HMP, the slope of the scattering curve at the low q range flattens significantly, indicating changes in the liposome bilayer structure.

Along with this, a significantly decreased intensity at low q range was observed for each sample with HMP added compared to the control sample. A Bragg diffraction peak was also observed around q=0.092 Å$^{-1}$ at an HMP concentration of 0.125% which shifts to slightly higher q and decreases in intensity with increased addition of HMP. The drop in scattering intensity at low q with the addition of more scattering entities (HMPs) and the observation of the Bragg peak are counter intuitive and are not easily fit using models for neutron scattering profiles. The drop in scattering intensity points to a decrease in the number density of the larger scattering entities (liposomes) and the Bragg peak demonstrates the occurrence of layered structures with relatively uniform spacing. But to better understand these SANS observations, cryo-TEM was used, and the imaging results for all samples used in SANS analysis are described below.

Results from Cryo Transmission Electron Microscopy of Microstructures

Figures 7A, 7B, 7C, 7D, 7E:
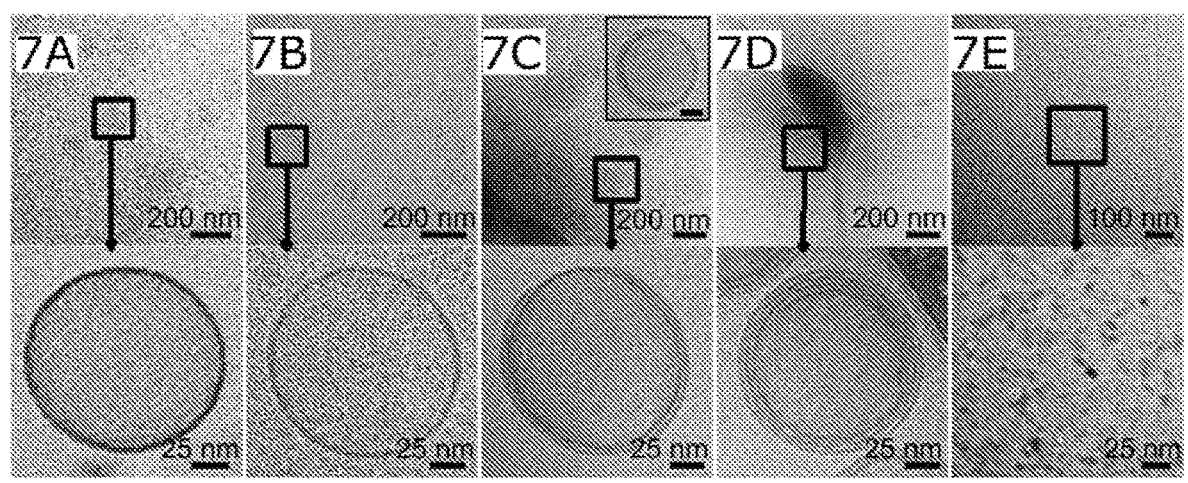
FIGS. 7A-7E show Cryo-TEM images at two levels of magnification for 0.25% liposome incubated in DI water (LIP, FIG. 7A), 0.25% UMP (LIP025UMP, FIG. 7B), 0.125% HMP (0125HMP, FIG. 7C), 0.25% HMP (LIP025HMP, FIG. 7D) and 0.5% HMP (LIP050HMP, FIG. 7E), in each image the corresponding high magnification image is depicted below for the region outlined with a square. While addition of UMP has no effect on the liposome structure, addition of HMP to liposome suspension results in a transition from unilamellar structure to two-bilayer (FIG. 7C) and multiple-bilayer (FIG. 7D) structures, and finally a solubilization of liposome (FIG. 7E). The inset in c indicates liposomes with multiple layer structures also exist in LIP0125HMP sample but with a small population. Scale bar of the inset is 50 nm.

FIG. 7A and FIG. 7B show cryo-TEM images of the control samples containing liposomes alone (FIG. 7A) and liposomes incubated with UMP (FIG. 7B) where higher resolution imaging was used to verify the unilamellarity of the liposomes. The clear observations are that the unilamellar PC liposomes are unchanged by the addition of UMP, in agreement with the SANS results. The liposomes are stable in the presence of UMPs, and the liposome-UMP interactions do not affect liposome structure.

The cryo-TEM images of liposomes incubated with varying concentrations of HMP are depicted in FIGS. 7C-7E. With 0.125% HMP addition, while there is no significant change in the size of liposomes, there is the interesting visualization of a second lipid layer, with higher resolution images showing that the layer is incomplete. We also observe liposomes with multiple bilayers (FIG. 7C). With cryo-TEM it is not possible to determine the number density of imaged objects as number density varies at different locations on the grid. Nevertheless, we observed a reduced density of liposomes over the TEM field of view. The observation of a reduced number density becomes more pronounced with the addition of HMP to a concentration of 0.25%, and again we see the presence of liposomes with multiple bilayers (FIG. 7D). In all these cases, the number of bilayers varies, and the formed additional layers are not necessarily complete and uniform. The average distance between each two adjacent layers (center to center distance) in the high magnification image of FIG. 7D was measured using Nano Measure software. Multiple measurements were taken at different locations, and the results were averaged. The measured average spacing distance is 6.8±0.9 nm, which agrees very well with the observed Bragg peak at a q value of 0.092 Å corresponding to a d spacing of 6.8 nm. To our knowledge, this is the first observation of liposomes with two or more bilayers with a relatively uniform spacing of a few nm.

When the HMP concentration is further increased to 0.5%, the SANS data shows the loss of the Bragg peak (curve e in FIG. 6A). On the cryo-TEM, no liposomes were observed in the TEM field of view indicating a complete disassembly of liposomes. However, clear evidence of small nanoscale structures was observed (FIG. 7E). A close examination of the images reveals that some of the shapes in the 2-D image appear somewhat circular with dimensions around 5 nm, and some appear elongated as small wormlike structures with a 5 nm thickness and a length of 10-15 nm. The circular dots typically have a higher contrast perhaps indicative of a coiled globular structure or of rods vitrified with axes parallel to the beam. The scattering curve at this HMP concentration can be again modeled through the Flexible Cylinder model (Table 1). The $R_g$ value calculated from the model fitting result is 5.1 nm, while the Guinier plot (inset to FIG. 4) shows the $R_g$ value of 4.7 nm and we note that these values are much smaller than liposomal dimensions but appreciably larger than the values for UMP and HMP alone. These suggest that the liposomes are converted into such new nanoscale structures upon addition of HMPs.

Both SANS and cryo-TEM reveal the important observation that HMP disrupts liposomes and at sufficiently high concentrations completely disassembles these vesicular structures. But most importantly, it is an additional conclusion that at intermediate concentrations, the HMPs induce the liposomes to fuse which leads to the creation of two or more bilayer structures on surviving liposomes. It is the formation of such multilayer liposomes that can give rise to the Bragg peak in the scattering.

While the above results relate to equilibrated samples, cryo-TEM makes it possible to gain an understanding of the dynamics of the structural transformations by contacting the liposomes with HMP and rapidly vitrifying the systems at varying incubation times. Thus, 0.25% liposome was incubated with 0.25% HMP (LIP025OHMP) for 1 min, 20 min, and 45 min after which they were vitrified for cryo-TEM imaging. The sample incubated for 1 min showed significant deformation evidence was observed demonstrating the formation of two bilayer structures and liposome rearrangement. At this stage, while the liposomes were multilayered, the spacing between bilayers was not uniform and considerably larger than the equilibrium value. At 45 min, liposomes with multi-layered structure were observed with the bilayer spacing down to ~7 nm. This result demonstrate that the formation of multilayer liposomes undergoes a stepwise process. After HMP incorporates in the bilayers, liposomes first partially break up and form open bilayer structures or large sheets (incomplete liposomes). The incomplete liposomes attach to surviving liposomes through hydrophobe insertion into bilayers to form multilayer structures. HMP thus serves as a connective material between the liposome bilayer and additional bilayers. This is distinctly different from small molecule surfactants (with single hydrophobic tail) that simply fluidize and eventually break up liposomes into mixed micelles of surfactant and lipid.

The identical experiments was performed but with 0.5% HMP (LIP05OHMP). Within 1 minute of mixing, broken liposomes with open structures are observed. After 20 min of incubation, the coexistence of small fragments and debris was observed. With 45 min of incubation, a complete breakdown of the liposomes occurred with the same suspended nanoscale structures observed as in FIG. 7E.

Figure 8A:
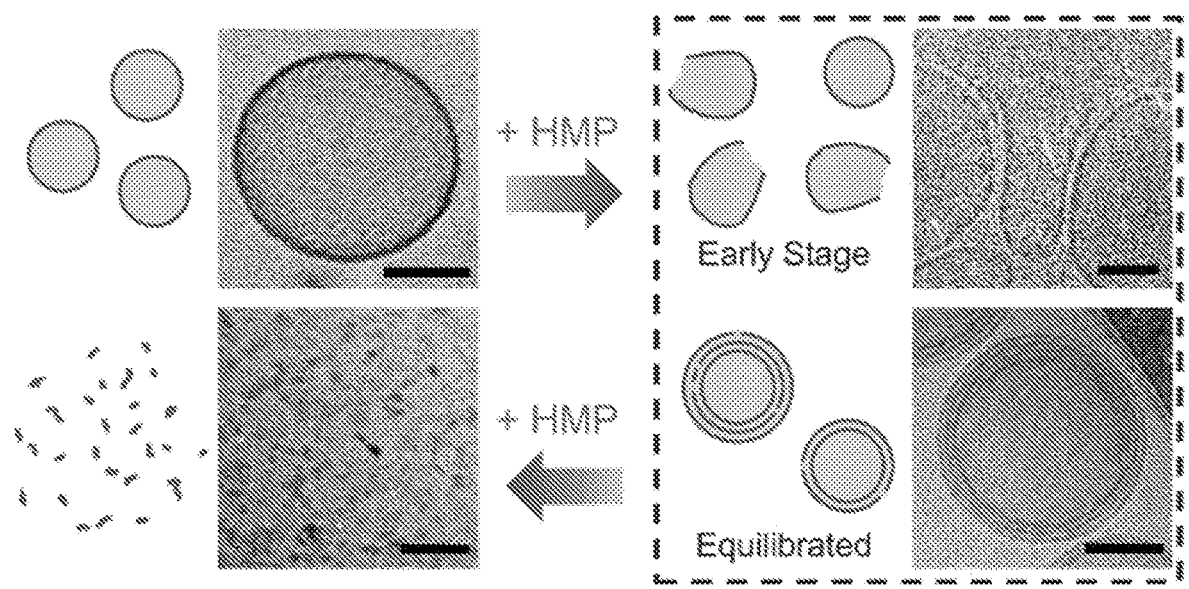
FIG. 8A is a schematic of the formation of multiple-bilayer liposomes and the solubilization of liposomes induced by HMP (scale bars in all the images are 50 nm).
Figure 8B:
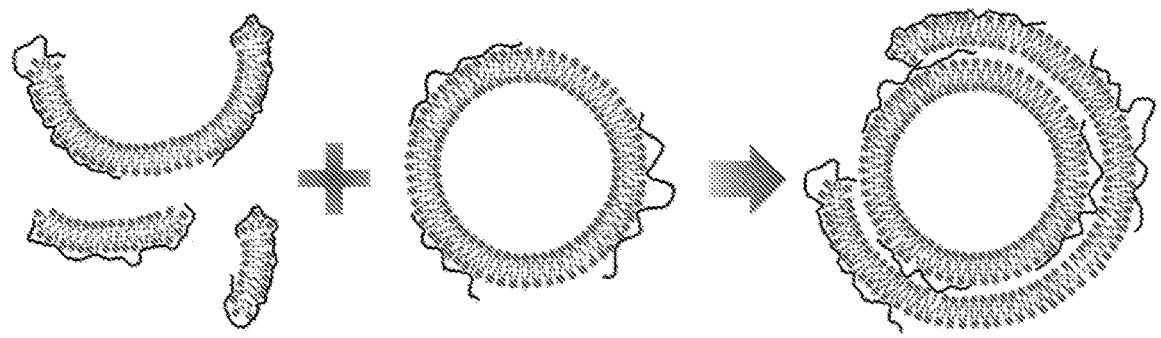
FIG. 8B is an Illustration of HMP bridging the fragments and lipid bilayer of a liposome by hydrophobe insertion forming two-bilayer structure.

Based on the SANS and cryo-TEM observations the mechanism for the results of liposome-HMP interactions are depicted in FIGS. 8A-8B. At the lower HMP concentrations, a fraction of the liposomes is broken into large fragments by the insertion of hydrophobes that have a sufficient local concentration in the bilayer to fluidize and disrupt the bilayer. Such softening of lipid bilayers through hydrophobe insertion is considered the dominant mechanism of liposome disruption by surfactants where the traditional model involves dissolution of liposomes into mixed lipid-surfactant micelles. Polymeric hydrophobes-containing amphiphiles such as HMPs are clearly distinct as they can bridge between lipid bilayers. Thus at the lower HMP concentrations, fragments with attached HMPs can reattach to remnant intact liposomes either through insertion of some of the free hydrophobes into the bilayer of intact liposomes or through interaction with other HMP chains that may be attached to the unbroken liposome (FIG. 8B). We propose that the attachment of these fragments may continue to the formation of multiple layers and the spacings are sufficiently periodic to give rise to the constructive interference in neutron diffraction leading to the observed peak at a d spacing of 6.8 nm. At high HMP concentrations, incorporation of additional HMPs into lipid bilayers results in a solubilization of lipid bilayers by forming lipid-HMP small elongated structures that are modeled by flexible cylinders.

Figure 9A:
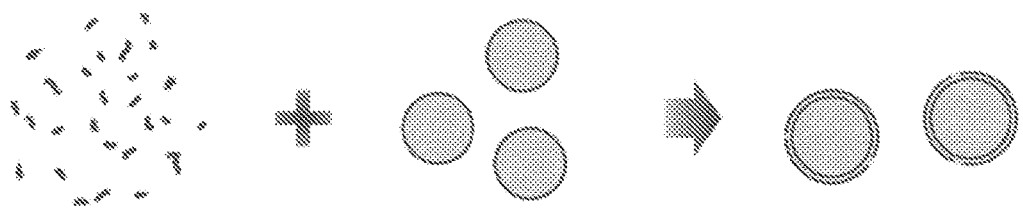
FIG. 9A is a schematic of the experiment showing addition of a lipid-HMP complex solution (LIP050HMP) to a fresh liposome suspension (LIP) at a volume ratio of 1:2.
Figure 9B:
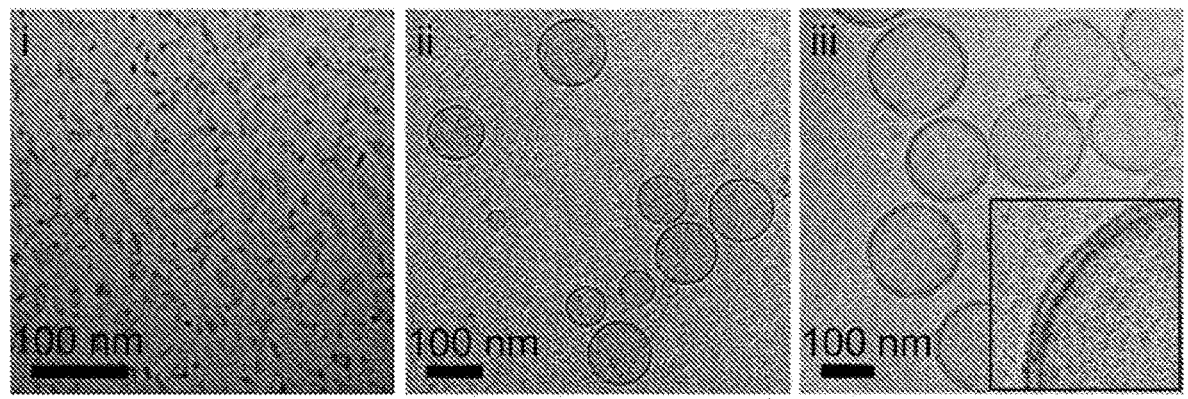
FIG. 9B shows cryo-TEM images of, from left to right, lipid-HMP complex (i), fresh liposome (ii) and reconstructed bilayers on bare liposomes (iii), with the inset depicting the reconstructed bilayer on liposome.
Figure 9C:
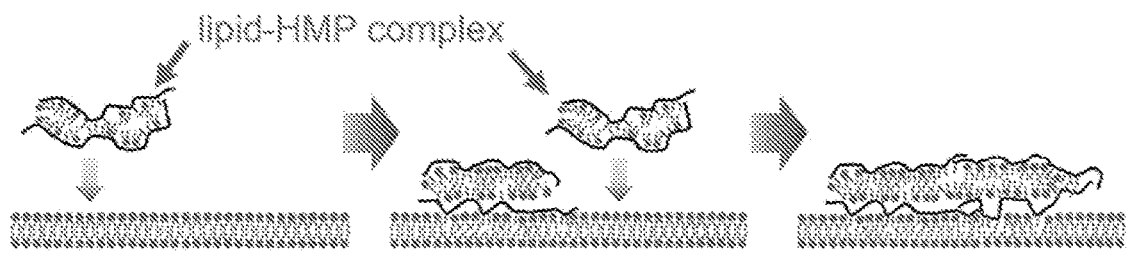
FIG. 9C is a schematic of building up bilayer structure from lipid-HMP complexes. When the lipid-HMP complexes contact bare liposomes, HMP incorporates into the bilayers by hydrophobe insertion into the fresh bilayers. The assembly of such attachment results in formation of additional lipid bilayers.

To demonstrate that fragments with the hydrophobes containing polymer can be hooked on to lipid bilayers the reverse experiment was performed by contacting the completely broken down liposome system as shown in FIG. 7E with a suspension of fresh intact liposomes The experiment was carried out by mixing the LIP050HMP solution with a fresh batch of liposomes (LIP) at a volume ratio of 1:2 (FIG. 9A). Incomplete layers formed on the surface of the new liposome, and it was difficult to visualize any remaining broken up structures (FIG. 9B). The two-bilayer structure is therefore reconstructed. The continuity of the second layer demonstrates the possibility of surface diffusion of the fragments that first attach to the intact liposomes and that upon contact, connect to each other through hydrophobe insertion (FIG. 9C).

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim:

1. A composition comprising a hydrophobically modified polypeptoid;
    wherein the hydrophobically modified polypeptoid is noncovalently associated with at least one lipid or lipid fragment of a liposome;
    wherein the hydrophobically modified polypeptoid is a random copolymer having a structure according to Formula I:

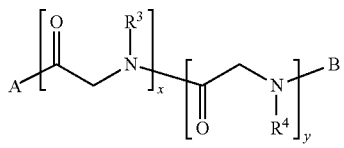

Formula I wherein x and y are positive integers such that x+y is about 12 to 300,
wherein A is a substituted or unsubstituted aryl or alkyl group,
wherein B is a hydrogen,
wherein $R^3$ is a methoxyethyl substituent, and wherein $R^4$ is selected from the group consisting of lauryl, stearyl, behenyl, and cetyl.

2. The composition of claim 1, wherein x is about 50 to 80, and wherein y is about 15 to 25.

3. The composition of claim 1, further comprising a hydrophobic drug.

4. The composition of claim 1, wherein the composition comprises two or more lipid bilayers, the composition further comprising:
    a liposome comprising a first lipid bilayer forming an interior region and an exterior surface, wherein a plurality of the hydrophobically modified polypeptoids is on the exterior surface of the liposome;
    wherein the plurality of the hydrophobically modified polypeptoids bridges a first lipid bilayer and a second lipid bilayer; and
    a hydrophilic drug in the interior region.

5. The composition of claim 4, further comprising a hydrophobic drug, wherein the hydrophobically modified polypeptoids on the surface of the liposome encapsulate the hydrophobic drug.

6. The composition of claim 4, wherein the composition comprises a multilamellar liposome comprising a plurality of lipid bilayers, wherein each lipid bilayer is connected to a next lipid bilayer by a plurality of the hydrophobically modified polypeptoids bridging two layers.

7. A composition comprising a hydrophobically modified polypeptoid and a lipid or lipid fragment, wherein the hydrophobically modified polypeptoid and lipid or lipid fragment form a complex derived from disruption of a liposome or vesicle;
    wherein the hydrophobically modified polypeptoid is noncovalently associated with at least one lipid or lipid fragment of a liposome;
    wherein the hydrophobically modified polypeptoid is a random copolymer having a structure according to Formula I:

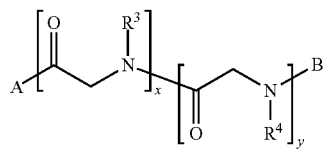

Formula I wherein x and y are positive integers such that x+y is about 12 to 300,
wherein A is a substituted or unsubstituted aryl or alkyl group,
wherein B is a hydrogen,
wherein $R^3$ is a methoxyethyl substituent, and wherein $R^4$ is selected from the group consisting of lauryl, stearyl, behenyl, and cetyl.

* * * * *